United States Patent
Mulligan et al.

(10) Patent No.: US 10,057,615 B2
(45) Date of Patent: Aug. 21, 2018

(54) SYSTEM AND METHOD FOR SCHEDULING AND CONTROLLING THE DISPLAY OF MEDIA CONTENT

(71) Applicants: David Grice Mulligan, Clinton, MD (US); Van Quoc Dang, Washington, DC (US)

(72) Inventors: David Grice Mulligan, Clinton, MD (US); Van Quoc Dang, Washington, DC (US)

(*) Notice: Subject to any disclaimer, the term of this patent is extended or adjusted under 35 U.S.C. 154(b) by 186 days.

(21) Appl. No.: 15/176,481

(22) Filed: Jun. 8, 2016

(65) Prior Publication Data

US 2017/0171581 A1 Jun. 15, 2017

Related U.S. Application Data

(60) Provisional application No. 62/267,519, filed on Dec. 15, 2015.

(51) Int. Cl.
| | |
|---|---|
| *H04N 7/173* | (2011.01) |
| *H04N 21/262* | (2011.01) |
| *H04N 21/845* | (2011.01) |
| *H04N 21/23* | (2011.01) |
| *H04N 21/214* | (2011.01) |
| *H04N 21/643* | (2011.01) |
| *H04N 21/482* | (2011.01) |

(52) U.S. Cl.
CPC ....... *H04N 21/262* (2013.01); *H04N 21/2143* (2013.01); *H04N 21/23* (2013.01); *H04N 21/4821* (2013.01); *H04N 21/64322* (2013.01); *H04N 21/845* (2013.01)

(58) Field of Classification Search
None
See application file for complete search history.

(56) References Cited

U.S. PATENT DOCUMENTS

| | | | | |
|---|---|---|---|---|
| 6,434,621 | B1 * | 8/2002 | Pezzillo | H04N 7/17318 348/E7.071 |
| 7,668,936 | B1 * | 2/2010 | Krikorian | H04N 5/44543 707/705 |
| 2001/0052000 | A1 * | 12/2001 | Giacalone, Jr. | G06Q 30/02 709/218 |

(Continued)

*Primary Examiner* — Kenny S Lin

(57) ABSTRACT

Systems and methods are provided herein for facilitating the scheduling and controlling the presentation of media content at one or more Venues (e.g., bars, restaurants). The scheduling and presentation is coordinated by a distributed system including a scheduling management server and a local subsystem at the Venue. The system is also configured to receive information from remote devices including electronic media guides as well as user devices enabling venue managers or the public to interact with the system. The system is configured to maintain a content presentation schedule and coordinate presentation at a Venue based on parameters obtained from remote devices including: the requirements of the Venue, requests from Patrons, programming available for presentation and the availability of resources at the venue (e.g., televisions). Moreover, the exemplary system is configured to implement/execute the schedule in view of the specific technological systems and requirements of the Venue's particular media presentation systems.

27 Claims, 12 Drawing Sheets

(56) References Cited

U.S. PATENT DOCUMENTS

| | | | | |
|---|---|---|---|---|
| 2003/0216958 A1* | 11/2003 | Register | ................ | G06Q 30/02 |
| | | | | 705/14.61 |
| 2004/0128198 A1* | 7/2004 | Register | ................ | G06Q 10/10 |
| | | | | 705/14.49 |
| 2009/0222392 A1* | 9/2009 | Martin | ................ | G11B 27/105 |
| | | | | 706/46 |
| 2011/0270948 A1* | 11/2011 | Zmuda | ................ | G06Q 20/10 |
| | | | | 709/217 |
| 2016/0021157 A1* | 1/2016 | Duerring | ............. | H04L 67/325 |
| | | | | 709/231 |

* cited by examiner

↓ Continued

350
Venue user employs functionality provided by the Program-to-Display Schedule Manager to schedule content onto display devices, indicating which programs the Patron-to-Display Reservation Manager may automatically change, interrupt, or supercede in response to program requests submitted by patrons.

355
Program-to-Display Schedule Manager populates empty time slots in the program-to-display schedule with program(s) scheduled to be broadcasted or available on the same channel or via the same source as the previous program that appears on the program-to-display schedule for the specific display device. If no program is available via on the same channel or via the same source as the previous program that appears on the program-to-display schedule for the specific display device, the time slot in the program-to-display schedule alerts the venue user that no content is currently scheduled for a specific time slot for a specific display device.

360
The Program-to-Display Schedule Manager updates the program-to-display schedules recorded in the Program-to-Display Database.

365
The Schedule Conflict Manager:

Identifies cases where a requested program cannot be presented in its entirety due to previously scheduled, higher priority programs.

Identifies cases where a requested program cannot be presented in its entirety because of a lack of content sources and/or display devices to support the display of the program at the requested time and/or location.

FIG. 3D

405
Patron Log-on or initial registration.

410
Patron uses Patron App or Patron Portal to identify available venue(s). Venues can be identified either within a specified radius of the user's current location, or by venue name, or by entering a city name or state name or zip code or address, or by entering keywords into the search function. After selecting a venue from the list, Patron can review the full EPG results for that venue and/or display schedules for any or all participating display devices at the venue.

415
Patron uses Patron App or Patron Portal to identify available content, and can narrow the EPG results using filters for any or all of program genre, team name, league name, date, time, live/recorded earlier, or by entering keywords into the search function. After narrowing EPG results to one or more programs, Patron can see a list of venues that have included those programs in one or more display schedules.

420
If Patron identifies a program scheduled for display at a venue, Patron can create a reservation to watch the program at the venue by clicking the "Make Reservation" button.

425
If Patron clicks the "Make Reservation" button, the Patron-to-Display Reservation Manager communicates an updated status of the specific program-display intersection to the Program-to-Display Schedule Manager, which in turn updates the status of the program-display intersection in the Program-to-Display Schedule Database. The Patron-to-Display Reservation Manager also updates the Patron-to-Display Reservation Database to reflect the new reservation, and confirms the reservation to Patron.

430
If the Patron arrives at the venue in accordance with the reservation, the Patron can check in at the Venue via the Patron Portal or Patron App to confirm that Patron has honored their end of the reservation. Alternatively, Patron can communicate their arrival directly to Venue staff who can update the reservation via the Venue Portal or Venue App.

FIG. 4B

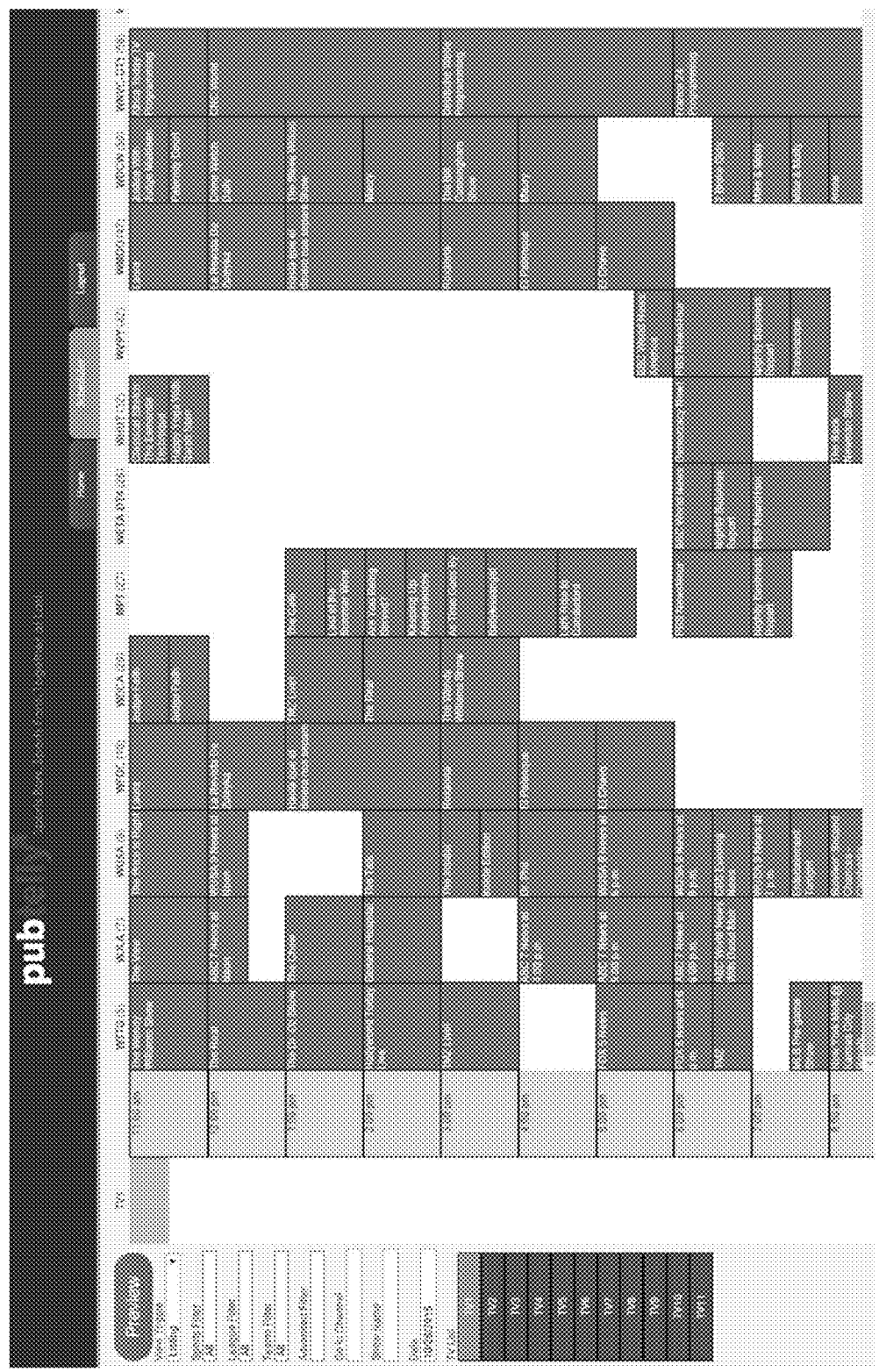
FIG. 5A Listing View within the Content-to-Presentation Schedule Manager

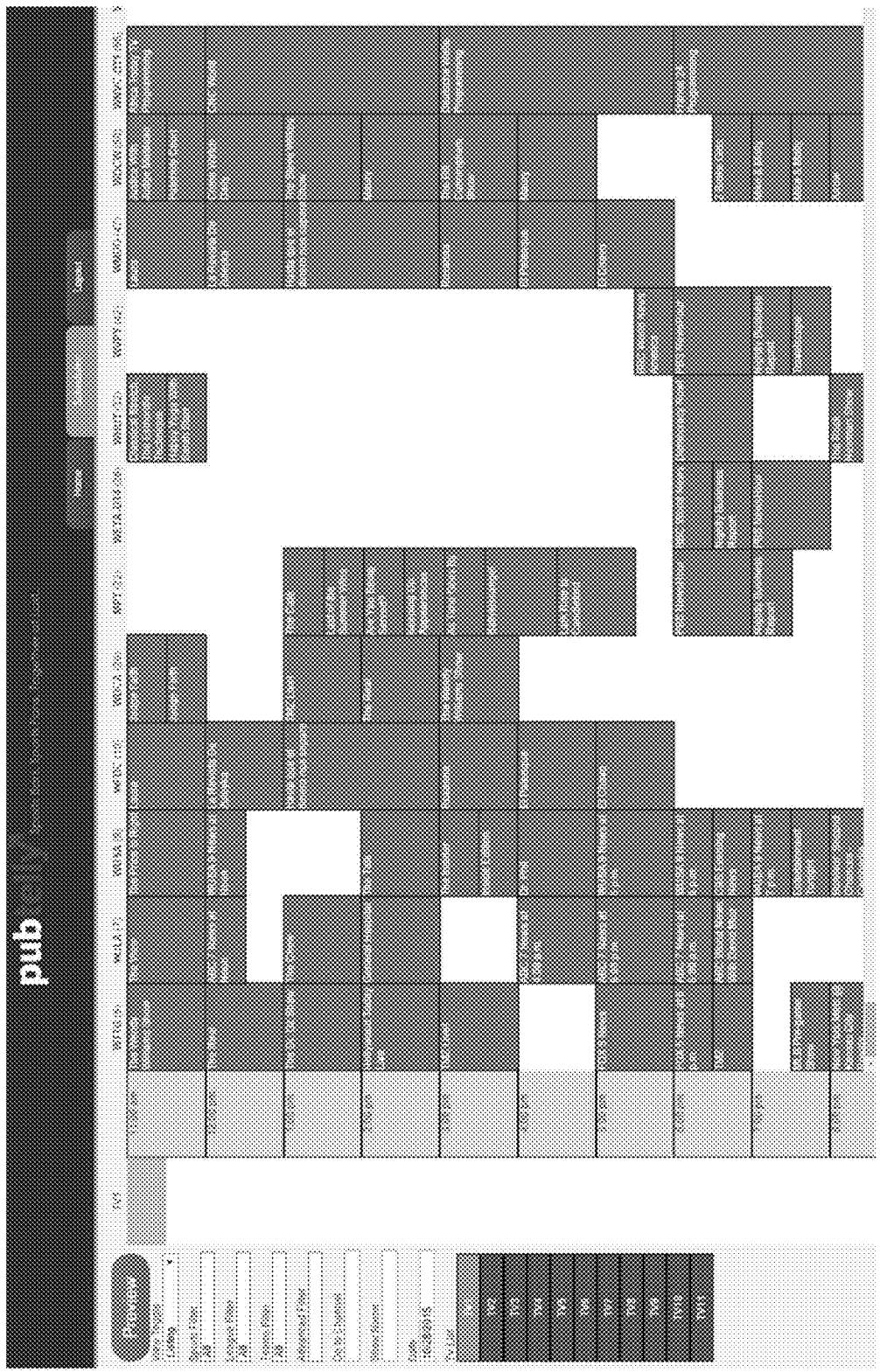
Device View within the Content-to-Presentation Schedule Manager. FIG. 5B

630
The system server communicates channel change requests to individual display devices by sending an encrypted channel change request to the specific Widget that is installed inside the specific Venue's private network to which the specific display device is connected.

635
The Widget converts the encrypted channel change request to a channel change request that is understood by the set top box, matrix switch, or other media management device that controls the content presented on the display device.

640
At a specified time, widget transmits the channel change request to one or more presentation devices, media mangement system and/or content sources

FIG. 6B

SYSTEM AND METHOD FOR SCHEDULING AND CONTROLLING THE DISPLAY OF MEDIA CONTENT

CROSS-REFERENCE TO RELATED APPLICATIONS

The present application is related to and includes U.S. patent application Ser. No. 62/267,519, entitled "SYSTEMS AND METHODS FOR SCHEDULING AND CONTROLLING THE DISPLAY OF MEDIA CONTENT" filed Dec. 15, 2015.

TECHNICAL FIELD OF THE INVENTION

The present invention relates to systems and methods for scheduling and controlling the presentation of media content, in particular, systems and methods for scheduling and coordinating the visual presentation of media content at a venue that includes a plurality of media presentation devices.

BACKGROUND

Restaurants, sports bars, sports clubs, and recreation facilities, among other establishments (collectively referred to as Venues), have historically invested in the installation of televisions, radios, Internet-enabled devices, and other audio and/or video devices and systems in an attempt to attract Patrons based on the assumptions that the presentation of media content will attract Patrons to the Venue, and/or capture the attention of visiting Patrons, thereby increasing the likelihood of Patron visits, and/or extending the average duration of Patron visits, with the increased Patron visits and/or extended Patron visit duration leading to increased consumption and increased Venue revenues. Venue investments in audio video equipment, media subscriptions, and media libraries have risen dramatically over the course of the past 20 years. Sports bars and sports themed restaurants often have 60 or more televisions, with expensive matrix switches installed to ensure that any television within the Venue can present any program for which the Venue has access via their media subscriptions. Some Venues have invested in expensive content management systems in an effort to simplify the use and/or coordination of the Venue's audio and/or video devices, media sources, and network infrastructure. Many Venues incur significant periodic expenditures attempting to communicate to the public the details and/or scope of their Venue's audio visual systems and/or media subscriptions in hopes that doing so will attract Patrons to their Venue.

Despite these investments in devices, network infrastructure and media subscriptions, and despite these periodic expenditures on marketing efforts, Venues are largely ineffective and inefficient at enabling existing and prospective Patrons to: (a) search for and identify the full range of specific media content an individual Venue intends to present for the upcoming two weeks; (b) search for and identify the full range of specific media content an individual Venue is capable of presenting for the upcoming two weeks; (c) search for and identify Venues that are willing and able to present media content that meets the Patron's interests; (d) create a reservation to enjoy specified media content via a Venue's device where the specified media content will be presented at a specified date and time during the upcoming two weeks; (e) other benefits for Patrons as described herein.

Additionally, despite these investments in devices, network infrastructure and media subscriptions, and despite these periodic expenditures on marketing efforts, Venues are largely ineffective and inefficient at: (a) developing detailed media content presentation schedules for their devices for the upcoming period; (b) automating the presentation of any and all scheduled media content on the respective devices for the upcoming period; (c) making the detailed media content schedules for the upcoming period available for discovery by prospective and existing Patrons; (d) enabling existing and prospective Patrons to interact with the Venue's media content presentation schedules in such a fashion that the Venue can determine which media content is of interest to existing and prospective Patrons; (e) other benefits for Venues as described herein.

Restaurants and bars often have subscriptions to specialized content packages that most individuals would not have at home, such as televised sports packages that are specific to one or more related sports or genres of content, so most Patrons will not have detailed knowledge of the content options available at a Venue without inquiring with the Venue directly. Therefore, it is also highly unlikely that a Patron will be able to accurately predict which of the unknown content would be appealing in the moment.

In cases where a prospective Patron is at home or out and about and has a specific event, program, or genre of media content in mind, the prospective Patron often doesn't know which Venues in the area are currently presenting or planning to present that content on their devices. The prospective Patron could use a telephone to call individual sports bars and restaurants until the Patron connects with a bar or restaurant staff person who has the time, ability and willingness to investigate whether the Venue's content subscriptions and devices are capable of supporting, and available to present the Patron's requested event, program, or genre of media content, and rely on that Venue representative to make a note regarding the Patron's requested program content and the Venue representative's agreement with the Patron to present the requested program content if and when the requesting Patron arrives at the Venue, and hope that all other Venue staff will read and be willing and able to honor the note, but that's an inefficient and ineffective process for both the prospective Patron and the Venue staff. The prospective Patron could also visit each Venue until he identifies a Venue that is capable of, and willing to present the content in which he is interested, and request that the Venue agree to present the content when it is broadcasted, streamed, or otherwise made available, and either stay at the Venue until the content is presented, or leave the Venue and return to the Venue on the date and at the time at which the content is due to be presented, and hope that the Venue representatives present at the Venue on that date and at that time are willing and able to honor the agreement to present the requested media content, but that's inefficient and ineffective as well. As a result, the prospective Patron often ends up doing something else. Ergo, the prospective Patron is not as happy, and a sports bar or restaurant in the area loses the prospective Patron's business.

Despite the fact that a sports bar might have 60 or more televisions, each of which could present one of several hundred simultaneously airing programs, there is no internet or telephone-based system that enables existing and prospective Patrons of restaurants and sports bars to search for a television program by genre, name, date, time and location such that the prospective Patron can reliably plan to view one or more television programs at a particular restaurant or sports bar.

Generally speaking, sports bars have multiple media sources, which may include a combination of cable, satellite, and/or Internet sources. Each media source can generally support the presentation of one program at a time, so if there are 8 media sources, there can be a maximum of 8 concurrent television programs presented across the sports bar's televisions. Many sports bars have in excess of 50 televisions. Channel changing and media-source-to-television mapping is generally performed manually and usually in real time. There are no records captured regarding the sports bar's planned program schedule, actual programs presented, the number of Patrons watching a specific program, food and beverage consumption by program, or Patron-specific data, including Patrons' preferences regarding program content, beverage choice, food choice, price elasticity, etc.

In most cases, the Venue's staff decides which programs are shown on a Venue's televisions. There are several problems with this approach. The public as a whole is not attending a specific sports bar, but rather individuals are attending a specific sports bar, and individuals have individual interests and preferences that differ widely from the public taken as a whole. If sports bars give their Patrons the ability to choose between all of the media content available from the sports bar's media subscriptions, Patrons will likely choose different programming than sports bar staff. Enabling Patrons to select the programming increases the likelihood that the Patron will be engaged by the programming, stay at the Venue longer, consume more of the Venue's product offerings, and have a better experience. There are two main barriers that Patrons must overcome before they ask for a change of media content.

The first, and most significant barrier, is a knowledge gap. The majority of Patrons don't know which media content is available, so they don't know what they can ask for. Venues do not offer their Patrons a media content menu detailing the broad array of media content offerings that could be made available via the Venue's media sources and presentation devices at any given moment. It would be much easier for the Venue to satisfy the Patron's media content appetite if the Venue could provide Patrons with a menu of all the current and upcoming media content that the Venue can offer.

In addition, most Patrons do not have the same media subscription packages that are carried by a restaurant. Also, a Patron's media content appetite is sensitive to the Patron's mood, the Patron's time availability, the nature of the Patron's visit, and other factors that cannot reasonably be predicted by the Venue's staff. Because most Patrons don't know their options, they take the path of least resistance and watch the programs the restaurant's staff chose. If a Patron isn't all that interested in those programs, he/she is less engaged, leaves sooner, and consumes less.

The second barrier is the avoidance of social debt. Individuals are generally hesitant to incur the social debt associated with asking restaurant staff to perform tasks without compensation and/or outside the scope of the staff's generally defined duties. Asking restaurant staff to search for content or change the channel takes the staff away from their clearly defined duties, exposes the requesting Patron to possible scorn or ridicule by other Patrons and staff, and has the potential to upset other Patrons. Not surprisingly, most Patrons won't ask for a change of television programming even if they know the specific program and channel they want to watch. This is especially true for female Patrons. This is costing restaurants and bars money. For regular Patrons, the social debt issue isn't all that significant, but for new or infrequent Patrons, social debt is a real issue. And it's the preferences of new and infrequent Patrons that Venue staff are least likely to know, and most important to satisfy, as those Patrons are the least comfortable. Getting those Patrons engaged and comfortable will tend to increase the length of their stay and the quantity of their consumption.

Venue owners invest in specialized employee training efforts to ensure that some Venue employees are available to operate the Venue's complex content management system. Employee turnover in the restaurant industry is relatively high, as is absenteeism. The complexity of the content management systems combined with employee turnover and absenteeism cause restaurants to incur unreasonably high costs, while the training efforts simultaneously fail to address the issues of the Patron's knowledge gap and the Patron's preference to avoid social debt.

Variety is the spice of life. It's also very effective at keeping Patrons engaged and increasing restaurant revenues. Currently, changing channels frequently in an effort to show a wide variety of programs is a time consuming, challenging process that's difficult to coordinate. By enabling restaurant staff to see an entire day's worth of media programming, build and view schedules for individual presentation devices, view schedules for all of the Venue's devices in a single chart, and filter the available content by type, genre, sport, team, league, and live events vs pre-recorded, and by automating the media source tuning management, network routing management, and device input management based on the Venue's media presentation schedules, the systems and methods disclosed herein make it easy for restaurant staff to maximize the allocation of Patron-desired media content presented on the Venue's devices, thereby enabling the Venue to deliver a much broader array of media content via the same media presentation devices, and enabling the Venue to satisfy a much broader selection of Patrons' media content interests.

Although system's exist in the area of providing media content to Patrons at a Venue, those systems have limitations. For example, current cable television and satellite programming provider systems do not allow non-subscribers or unrelated third parties to schedule programs, nor do these systems allow unrelated third parties to view and filter the future program schedules for collections or cross-sections of their subscribers. Imagine a Patron has identified three local Venues to which the Patron is considering visiting, and each Venue has a collection of media subscriptions and services. There is currently no single system available that: (a) allows the Patron to view what media content each of the three Venues is planning to present on a specified future date and at a specified time; (b) allows the Patron to identify which of the Venues has a media content subscription package that includes a specific upcoming program; (c) allows the Patron to identify which of the Venues has a media content subscription package that includes a specific upcoming program and has unclaimed media presentation capacity to allow him to enjoy the specified program without interfering with the Venue's previously scheduled media content presentation plans; (d) allows the Patron to request the presentation of a specific program on a Venue's presentation device; (e) automatically schedules the requested media content to be presented on a specific device and provides the Patron with a confirmation that the content has been scheduled and will be presented on a specific device at the specified Venue at a specified time on a specified date.

There exist restaurant reservation systems with which Patrons can reserve a table at a restaurant, securing a time and location for a meal. However, such systems are limited as Patrons cannot use these systems to schedule the presentation of media content to coincide and co-locate with their table reservation. Nor do there exist content management systems that are configured to integrate with reservation systems.

There exist theater ticket systems with which a Patron can reserve a ticket to watch a movie on a specified date, and at a specified time and location. However, these systems have limited use and functionality as further described herein. A Patron can only select from the list of shows and show times that the theater has scheduled and published. The Patron cannot search a list of available shows that, though available, have not been scheduled for presentation by the theater, and subsequently submit a request for the unscheduled content and receive an automated response including a reservation for the presentation of the requested content. A large theater might have ten or more individual viewing rooms, with each viewing room presenting five to eight movies each day, for a maximum total of perhaps 100 movies per day. By contrast, a large spots bar might have 60 or more televisions, with each television capable of showing twenty television programs per day, for a maximum total of perhaps 1000 television programs per day. The theater reservation (ticket) generally allows the Patron to enter one viewing room for the duration of a single movie presentation, and individual movies are generally presented in closed viewing rooms, thereby precluding theater patrons from using a single reservation to watch multiple movies concurrently. By contrast, a Patron of a sports bar may enjoy media content presented on a variety of audio and video devices concurrently. The theater ticket is generally not transferrable to allow the Patron to watch a different movie being aired at the same time, and the theater reservation (ticket) is for a specified beginning and end time, not for an open ended 'visit'. By contrast, a Patron who visits a restaurant to eat dinner might become interested in a baseball game being presented on one video device and, having reached the conclusion of the baseball game, or having become disinterested in the baseball game, subsequently decide to focus attention on a golf match being presented on a different video device. Or the restaurant Patron might opt to enjoy both the baseball game and the golf match concurrently. A theater reservation (ticket) does not allow the Patron to reserve a showing of the 3rd and 4th hour of a 4-hour program, such as a golf match, leaving the presentation hardware (a viewing room and associated projection equipment in the case of a theater), free to be used by other Patrons for the beginning two hours of the program. By contrast, it is reasonable for a Patron to arrange with a restaurant to arrive at the restaurant with the express intent of watching the final two hours of a golf match, and for the restaurant to present other content to other Patrons using the same television during the first two hours of the golf match. A theater ticket doesn't generally afford the theater the option of changing the content to appease other Patrons if the ticket holder fails to appear at the Venue in accordance with the reservation agreement. By contrast, the reservation system described herein allows the restaurant to establish general reservation rules (for example, the Patron must arrive 10 minutes before show time, or be present when the show starts, or arrive within the first 10 minutes of the show's airing), or specific rules for specific programs (for example, Patrons might be allowed to arrive within the first hour of any program that is scheduled to last more than 3 hours.) Patrons arriving 40 minutes into the showing of a 3-hour movie at a theater are considered disruptive to other moviegoers. Patrons arriving 40 minutes into the showing of a 3-hour sports broadcast at a sports bar are de rigueur.

There exist content management systems, some of which allow restaurant staff to change channels on televisions via a network, thereby eliminating the need for remote controls. These systems do not, however, allow restaurant staff and outside Patrons to schedule extended periods worth of television programs on every television for future viewing, nor do they associate television reservations with individual Patrons and integrate with other systems such as table reservation systems.

It is with respect to these and other considerations that the disclosure made herein is presented. A non-exhaustive list of the issues addressed by the exemplary embodiments of the invention disclosed herein are as follows:

1. For organizations whose business model relies on the use of multiple presentation devices fed by multiple media sources to satisfy their Patrons' media content interests, there is no commercially available solution that enables the organization to:
   (a) schedule media content for multiple presentation devices fed by multiple media sources and be able to maintain, update and share the media presentation schedule(s) internally;
   (b) make the media presentation schedule(s) discoverable and searchable by the public via an Internet browser, software system, mobile device or app;
   (c) automate the issuance of tuning instructions to multiple media sources based on a single consolidated media presentation schedule or collection of media presentation schedules;
   (d) capture and respond to media presentation requests submitted by prospective and/or current Patrons, automatically updating the consolidated media presentation schedule visible to Venue staff and current and prospective Patrons;
   (e) collect and report on current and/or prospective Patrons' media content interests, thereby supporting proactive media scheduling and advertising, and proactive interactions with current and prospective Patrons;
   (f) relate Patrons' program interests to point-of-sale records, thereby supporting analyses of food and beverage consumption as related to media content, the effectiveness of advertising as it relates to specific media content, market penetration by product by media content, etc.
   (g) review the Venue's upcoming media presentation schedules to accurately predict patronage highs and lows, accurately plan food and beverage inventories, and proactively schedule special offers to lure Patrons during predicted periods of low patronage;
2. For Patrons whose interests include enjoying audio and/or video media and/or socializing while audio and/or video media are being presented, there is no commercially available solution that enables the Patron to:
   (a) search, sort and/or filter an electronic program guide/interactive program guide to identify media content programming that matches the Patron's interests, and identify the date and time the media content will be presented, and match that information with the location of Venue(s) that have scheduled to present the specific media content or have the ability to present the specific media content, based on the Venue's operating hours, media presentation schedules, audio/video network configuration(s), presentation device availability, and media subscriptions;

(b) submit an electronic request for the presentation of specified media content and receive an automated confirmation and associated reservation, or a rejection from the selected Venue;
(c) use their mobile device while in a Venue to request and achieve a change of media content being presented via the Venue's presentation devices;
(d) coordinate their visit to a Venue with other Patrons, including reserving seating, scheduling media presentations on the Venue's presentation devices, and coordinating invitations, acceptances, rejections, etc.;
(e) receive coordinated alerts, updates, and offers from Venues, content providers, teams, leagues, the beverage industry, and other related parties based on the Patron's stated preferences and historical behaviors;
(f) search for and identify a Venue or list of Venues that have scheduled to present specific media content or have the ability to present specific media content, and that simultaneously offer specific food and/or beverage options that meet the Patron's interests, i.e. specific beer on draft, specific beer in a bottle, type of beer (IPA, stout, pilsner, etc.), beer price, special pricing, special beverage offers, vegetarian food options, barbecue, etc.
3. For the beverage industry, there is no solution that enables the industry to:
(a) analyze directly, and in real time, the relationships between programming content, user consumption, pricing, special offers, location, Patrons' media content preferences and historical behavior, advertising, and other factors;
(b) analyze the relationships between a selected Patron's social network status, media content consumption in a specified Venue or Venues, and beverage consumption;
(c) analyze network effects involving their beverages;
(d) analyze the effectiveness of their sponsorship arrangements with, and advertising campaigns related to specific sports, teams, leagues, market segments, locations, geographic regions, and Venues.
4. For teams, there is no commercially available solution that enables teams to:
(a) get more detailed information regarding people who visit sports bars and/or restaurants with the express intent of enjoying media content related to their team, league and/or sport;
(b) analyze the effectiveness of their sponsor relationships with the beverage industry;
(c) identify, in advance, Venues at which large numbers of their fans or their competition's fans plan to enjoy media content that relates to their team, league and/or sport, thereby enabling teams to proactively engage Venues and Patrons.
5. For television networks and other media content providers, there is no product that enables television networks and media content providers to:
(a) analyze directly, and in real time, the relationships between programming content, user consumption, pricing, special offers, location, geographic region, Patron content preferences and historical behavior, advertising, and other factors;
(b) analyze the relationships between a selected Patron's social network status, media content consumption in a specified Venue or Venues, and consumption of advertised products and services;
(c) analyze network effects related to advertisements;
(d) analyze the effectiveness of advertising campaigns related to specific sports, teams, leagues, and market segments.

6. For content carriers (for example, DirectTV, Comcast, etc.), there is currently no product or solution that enables content carriers to:
(a) obtain and analyze details regarding Venues' Patrons' media content requests and populations served;
(b) obtain and analyze details regarding which Venues intend to show which television content up to two weeks prior to the airing of the content.

The systems and methods disclosed herein address each of the above issues and other considerations. The details of one or more implementations are set forth in the accompanying drawings and the description below. Other features and advantages will be apparent from the description and drawings, and from the claims.

BRIEF DESCRIPTION OF THE DRAWINGS

FIG. 3A-3D are flow diagrams that illustrate exemplary methods for scheduling and controlling the display of media content in accordance with one or more of the disclosed embodiments;

FIG. 4A-4B are flow diagrams that illustrate exemplary methods for scheduling and controlling the display of media content in accordance with one or more of the disclosed embodiments;

FIG. 5A-5B are diagrams illustrating exemplary graphical user interfaces in accordance with one or more of the disclosed embodiments; and FIG. 6A-6B are flow diagrams that illustrate exemplary methods for scheduling and controlling the display of media content in accordance with one or more of the disclosed embodiments.

SUMMARY OF THE INVENTION

Figure 1:
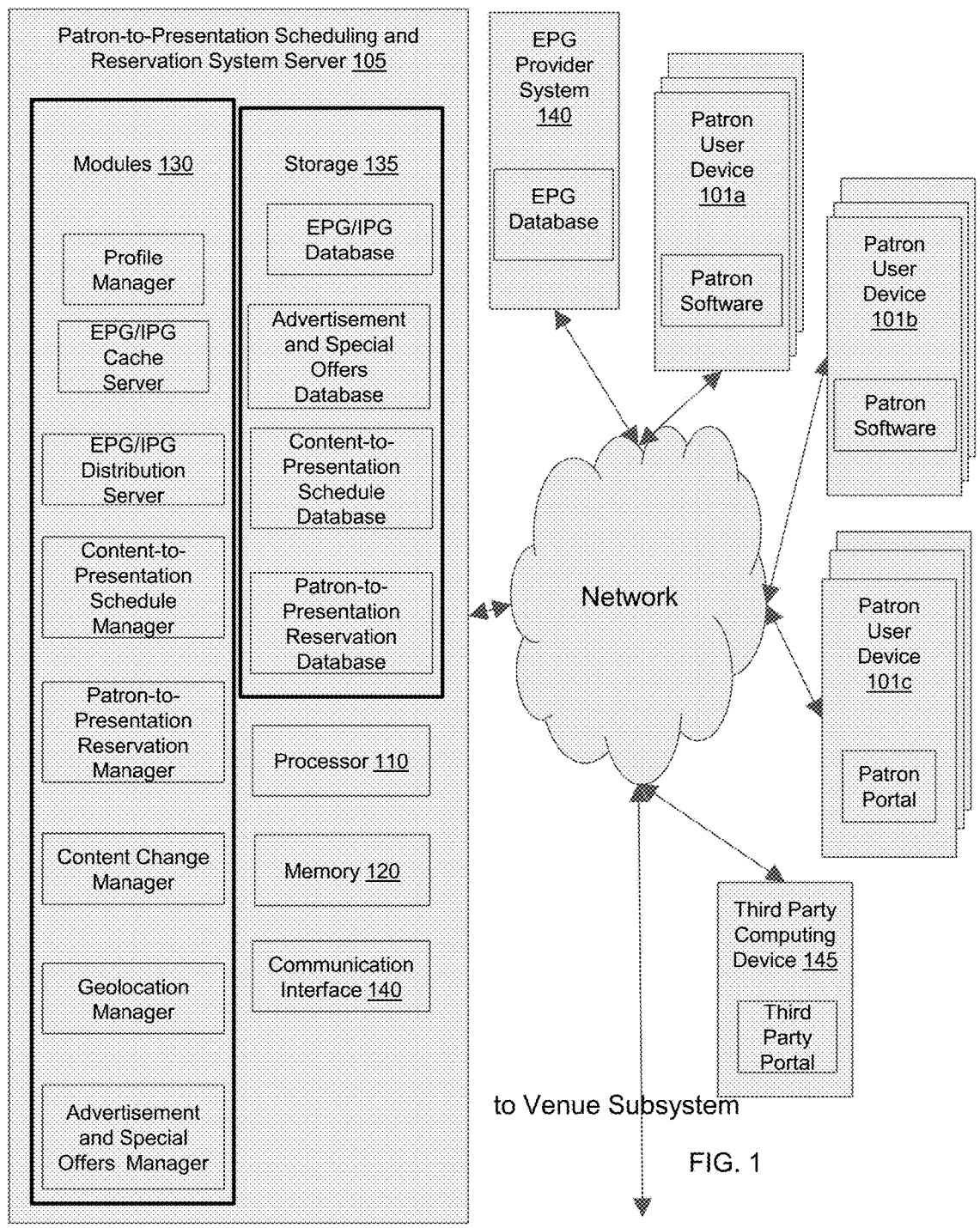
FIG. 1 is a high-level diagram illustrating an exemplary configuration of a system for scheduling and controlling the display of media content in accordance with one or more of the disclosed embodiments.

Technologies are presented herein in support of a system and method for scheduling and controlling the presentation of media content at a venue. According to a first aspect, a computer-implemented method for scheduling and controlling the presentation of media content at a venue is provided, wherein the venue has media devices including one or more media source devices connected to a network at the venue and connected to one or more media presentation devices. The method comprises, receiving at a schedule management server, electronic programming data including a list of media content items that are available for presentation at the venue, a respective media source and any respective time-periods for each of the media content items. Also received at the schedule management server is venue data including information identifying the one or more media source devices. It should be noted that the one or more media source devices are configured to provide media content received from a respective media source to one or more media presentation devices for output. The method also includes the step of providing a venue control module at the venue. The venue control module is provided for integration in the LAN and is configured to communicate with the one or more media devices via the venue network and communicate with the server via a communications network connection. The venue control module is one or more of: a device operatively connected to the venue network and a software module executed by one or more of the media devices which are operatively connected to the venue network. The method further includes the step of maintaining, with the server based on the electronic programming data and the venue data, a venue programming schedule identifying scheduled media content items for presentation at the venue during respective time periods. The method also includes the step of generating, according to the venue programming schedule, control instructions that cause one or more of the media devices at the venue to output the scheduled media content items at the venue during respective time periods. According to the method, the control instructions are generated by one or more of the schedule management server based on the venue data and the venue control module based on venue settings concerning a configuration of the media devices at the venue. The method also includes the step of providing the control instructions at the venue control module. In addition, the method includes the step of issuing, by the venue control module according to the control instructions, control parameters to one or more of the media devices, wherein the control parameters cause one or more of the media devices to transition to a respective state that is suitable for presenting a particular scheduled media content item at the venue at a respective execution time.

According to another aspect, a system is provided for scheduling and controlling the presentation of media content at a venue having a network of media devices including media presentation devices and one or more media source devices connected to a network at the venue. The one or more media source devices are configured provide media content received from a respective media source to one or more of the media presentation devices for output. The system includes a schedule management server comprising: a processor, a non-transitory computer readable storage medium and one or more software modules in the form of encoded instructions that are executable by the processor.

In addition, the software modules include a communications module that configures the schedule management server to receive electronic programming data and venue data from one or more remote computing devices over a communications network. The electronic programming data includes a list of media content items that are available for presentation at the venue, a respective media source and any respective time-periods for each of the media content items. In addition, the venue data includes information identifying the one or more media source devices at the venue. The software modules also include a scheduling module that configures the schedule management server to maintain, based on the electronic programming data and the venue data, a venue programming schedule identifying scheduled media content items for presentation at the venue during respective time periods. The software modules also include a content change manager that configures the schedule management server to transmit content change instructions based on the venue programming schedule over the communication network to a venue.

The system further includes a venue control module located at the venue for automatically coordinating the output of the scheduled media content items at the venue during respective time periods according to the venue programming schedule. The venue control module is integrated within the venue network and is configured to communicate with one or more of the media devices at the venue over the venue network and communicate with the schedule management server over the communications network. In addition, the venue control module is further configured to maintain, in a storage medium, venue settings concerning a configuration of the media devices at the venue. The venue control module is also configured to generate, according to the received content change instructions and the venue settings, control instructions that transition one or more of the media devices to a respective state that is suitable for presenting a particular scheduled media content item at the venue at a respective execution time. In addition, the venue control module is configured to transmit the control instructions to one or more of the media devices over the venue network.

These and other aspects, features, and advantages can be appreciated from the accompanying description of certain embodiments of the invention and the accompanying drawing figures and claims.

DETAILED DESCRIPTION

By way of overview and introduction, distributed systems and methods are provided herein for facilitating the scheduling and controlling the presentation of media content at one or more Venues. Venues, for example can include, restaurants, sports bars, sports clubs, and recreation facilities, among other establishments, and is often referred to herein as a "sports bar" although this particular term should be understood to be non-limiting. The scheduling and presentation is primarily coordinated by a distributed system including a back-end presentation scheduling and reservation system server (often referred to as the "pubtelly" server or system server), one or more subsystems that are local to the Venue, and one or more subsystems that are available to the public. As further described herein, the system can also include one or more additional front-end user facing devices or virtual portals that enable Venue-level operators or the public at large (e.g., Patrons or prospective Patrons) to access and interact with the system via a network such as the internet. Furthermore, the system is configured to integrate with and obtain information related to the available programming from various networked third-party computing systems associated with content providers and related electronic programming guide/interactive programming guide (EPG/IPG) systems.

As further described herein, scheduling and presentation is coordinated by the back-end server in conjunction with the Venue side systems and Patron side systems, and the system is configured to manage the scheduling and presentation of content within each Venue based on a variety of parameters obtained from the remote computing devices including, without limitation: the specific requirements of the Venue, requests from Patrons (e.g., one or more members of the public irrespective of whether they are affiliated with a particular Venue), the programming available for presentation at the Venue and the availability of content presentation resources (e.g., televisions at the Venue). Moreover, as further described herein, the exemplary media content scheduling and presentation control systems and methods are configured to implement/execute the schedule in view of the specific technological systems and requirements of the Venue's particular media presentation systems.

The system enables Venues to schedule every program on every presentation device in their Venue in advance (e.g., up to two weeks), and makes every media presentation in the schedule discoverable by the public. Additionally, the system enables the public to search for and identify media presentations that are included in the Venues' media subscription(s) and request that a Venue add those programs to their media presentation schedule if those media presentations are not already scheduled. Moreover, the system enables the public to create a reservation to enjoy one or more media presentations at a Venue. In addition, the reservation system enables the Venue to establish rules regarding how long the Venue will hold the reservation. Accordingly, the system integrates with the Venue's reservation systems or Patron facing social networks to determine whether a Patron is at the Venue as specified by a reservation (e.g., based on social network check-ins, status updates or patron device geolocation functionality) to verify the Patron has meet the reservation terms. For instance, the Patron must arrive 10 minutes before the program starts, or be in the Venue when the program starts, or arrive within 15 minutes after the programs starts. By way of further example, for longer programs such as a televised golf tournament, which may air for 4-6 hours, the Venue can create ad hoc reservation rules. By way of further example, as Patrons may only wish to watch the final 90 minutes of a 4-hour program, the exemplary system allows the Patron to indicate his/her expected arrival time. Unlike movie theaters, which have a fixed content schedule and limited offerings, the proposed systems and methods further described herein enable Venues to update their media presentation schedules in response to Patron requests as well as Patron conduct (e.g., purchasing within the establishment).

According to a salient aspect, the systems and methods described herein are further configured to automate the implementation of the schedule in accordance with the particular technical systems in place in the Venue. By automating channel changes, restaurant staff are freed up from navigating through a crowded restaurant with a remote control, changing a channel of a television that is actively being watched by other Patrons, leaning over dining Patrons to point the remote at a media receiver mounted on the back of a television high up on a wall, and inadvertently changing channels on other televisions when the remote's infrared signal finds its way to other media receivers. Moreover, as further described herein, the exemplary systems and methods for controlling the presentation of media content provides an automated system that integrates with and controls the various media sources, media management systems and presentation devices at the Venue and provides a technical solution that algorithmically modifies, supplements or oversees the various existing systems and processes at the Venue. As a result, the exemplary systems and methods address significant limitations of such existing systems including, inter alia, improving the operating efficiency of the existing systems, and enhancing the features and functionality through coordinated control and integration of these distributed and otherwise independent preexisting hardware and software-based systems.

Exemplary System Overview

An exemplary system for scheduling and controlling the presentation of media content 100 is shown as a high-level block diagram in FIG. 1. In this arrangement, the system 100 consists of a Patron-to-Presentation Scheduling and Reservation System Server 105 (referred to herein as the system server and/or pubtelly server). Also shown are remote computing devices in communication with the system server 105, over a network, including one or more Patron user computing devices 101a-101c, EPG provider computing device 140, and Venue Subsystem (150, shown in FIG. 2) and one or more third party user computing devices/systems 145. It should be understood that any of the remote computing devices depicted in FIG. 1 (or the one or more components of the system that exist within the Venue subsystem shown in FIG. 2) can be in direct communication with one-another or the system server 105, indirect communication with one-another or the system server 105, and/or can be communicatively coordinated with one-another or the system server 105 through a computer network, such as the Internet.

Patron User Device is intended to represent various computing devices and/or data processing apparatuses suitable to facilitate the operation of the system for scheduling and controlling the presentation of media content 100, including, but not limited to, a desktop computer, laptop computer, tablet computer, mobile phone, or other device capable of supporting the operations of either connecting to the Internet, or of supporting the operations of the Patron App and connecting to the Internet, or of supporting the operations of the Patron Software and connecting to the Internet. As further described herein, Patron device can be configured to collect information from respective Patrons, communicate the information to remote computing devices (e.g., system server 105, Venue subsystem) and receive information from the remote computing devices and display the information to respective Patron. As shown, the Patron user devices can be executing one or more client applications, including a Patron application. The Patron application is a software application comprising instructions in the form of code that, when executed by the patron user device processor (not shown), configures the device to collect information from the user, and provides the information to the system server 105 over the network in accordance with the exemplary methods further described herein. Although the Patron application is discussed herein as a stand-alone software application executing on respective user devices, it can be appreciated that the application can be executing on one or more remote server devices that are accessible by the user devices over a network. For instance, Patrons can interact with the various components of the system 100 via any device that can support a modern web browser and connect to the Internet. Alternatively, Patrons can access the Patron-to-Presentation Scheduling and Reservation System via any device onto which the Patron can install the Patron App, and which said device is capable of operating the Patron App and connecting to the Internet. Alternatively, Patrons can access the system 100 and interact with the various components (e.g., system server 105 or components within the Venue subsystem 150) via any device onto which the Patron can install the Patron Software, and which said device is capable of operating the Patron Software and connecting to the Internet.

As would be understood by those in the art, Electronic Program Guides (EPGs) and Interactive Program Guides (IPGs) are menu-based systems that provide users of television, radio and other media applications with continuously updated (menus displaying broadcast programming or scheduling information for current and upcoming programming. Non-interactive electronic program guides (sometimes known as "navigation software") are typically available for television and radio, and consist of a digitally displayed, non-interactive menu of program scheduling information shown by a cable or satellite television provider to its viewers on a dedicated channel. EPGs are transmitted by specialized video character generation (CG) equipment housed within each such provider's central headend facility. By tuning into an EPG channel, a menu is displayed that lists current and upcoming television programs on all available channels. A more modern form of the EPG, associated with both television and radio broadcasting, is the interactive [electronic] program guide (IPG, though often referred to as EPG). An IPG allows television viewers and radio listeners to navigate scheduling information menus interactively, selecting and discovering programming by time, title, channel or genre using an input device such as a keypad, computer keyboard or television remote control. Its interactive menus are generated entirely within local receiving or display equipment using raw scheduling data sent by individual broadcast stations or centralized scheduling information providers. A typical IPG provides information covering a span of seven or fourteen days.

EPG Provider System 140 is intended to represent one or more computing systems that are associated with EPG or IPG providers, for instance, an Electronic Program Guide/Interactive Program Guide Provider. An Electronic Program Guide/Interactive Program Guide Provider is third-party listings metadata aggregator that collects television or radio broadcast program information in a database, and may, at its discretion, update, modify, or otherwise change the content associated with the program information, including but not limited to, the description, tagging, and inclusion of individual programs in the EPG/IPG, and subsequently makes the EPG/IPG available to third parties in any of a variety of formats and or forms, including but not limited to XML, JSON, character delimited text, database, text, fax, Telex, Teletype, electronic download, application program interface ("API"), other electronic means, and/or via physical distribution in the form of compact disc, portable recording device, etc.

Data used to populate an EPG/IPG may be distributed over the Internet, via physical delivery in the form of compact disc, cassette, writable digital media, portable recording device, USB stick, paper, or other means, either for a charge or free of charge, and implemented on a computing system (e.g., EPG Provider System 140) connected directly or through a computer to the Internet.

Overview of the Venue Subsystem

Figure 2:
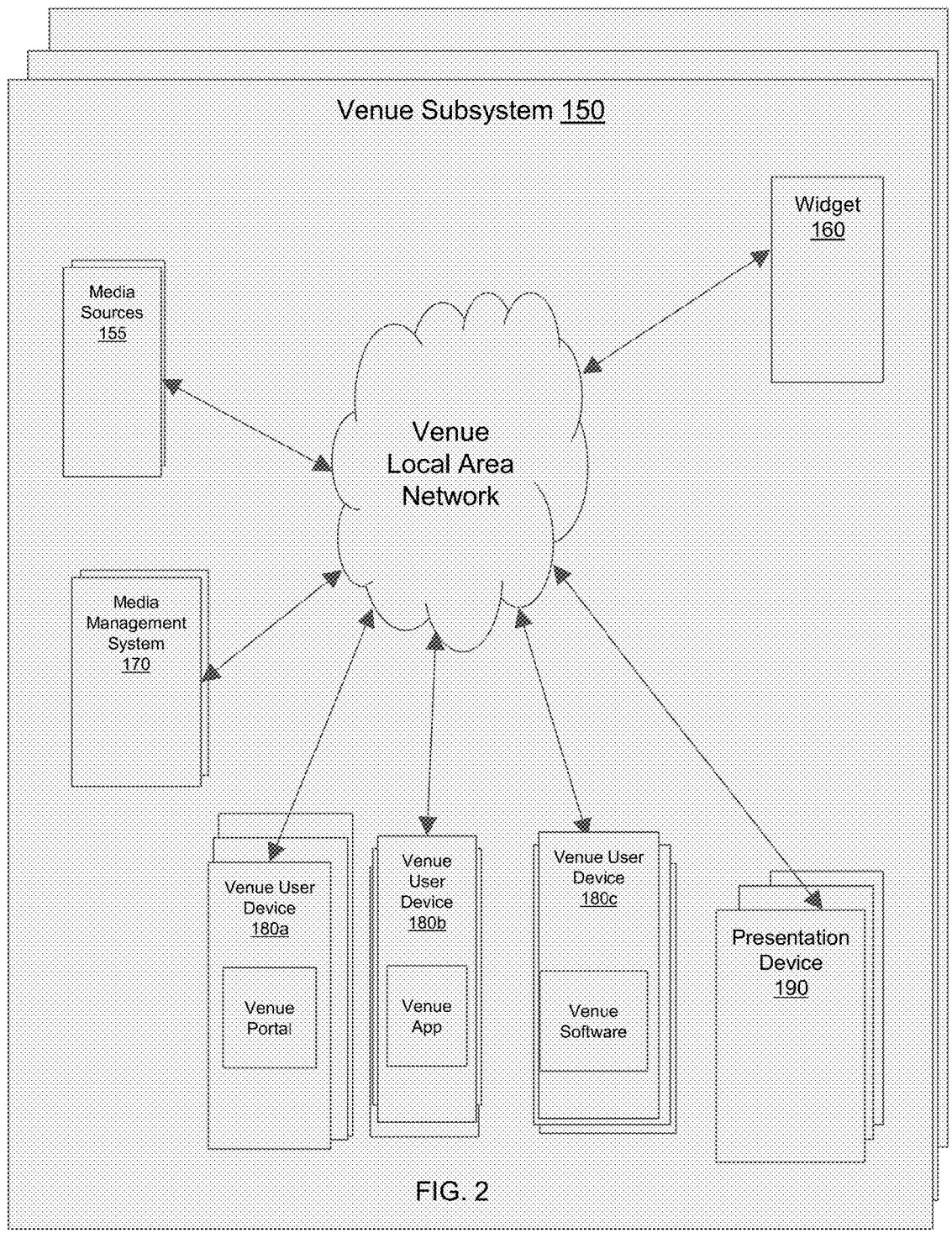
FIG. 2 is a high-level diagram illustrating an exemplary configuration of the system for scheduling and controlling the display of media content in accordance with one or more of the disclosed embodiments.
Figure 3A:
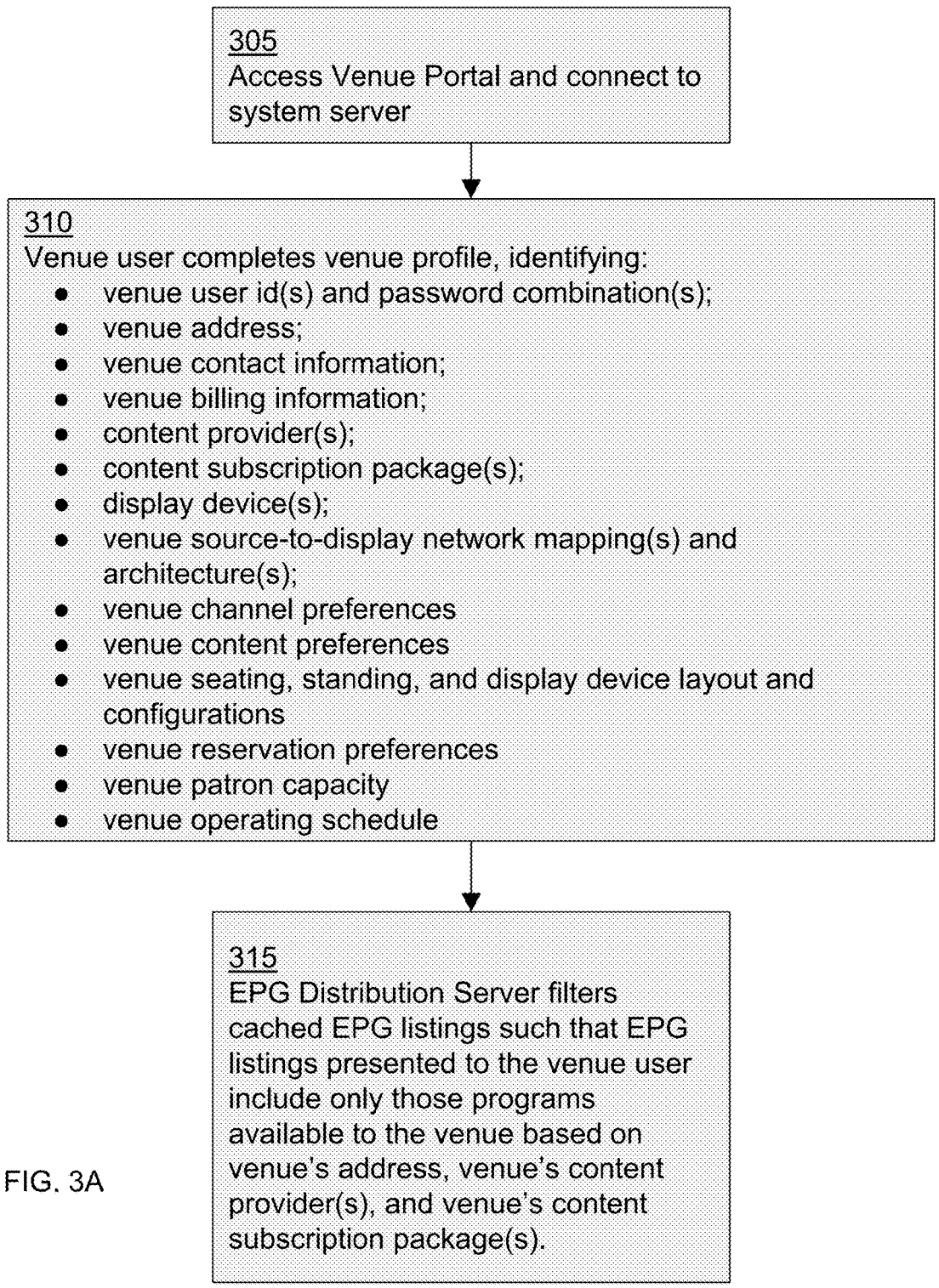
Figure 3B:
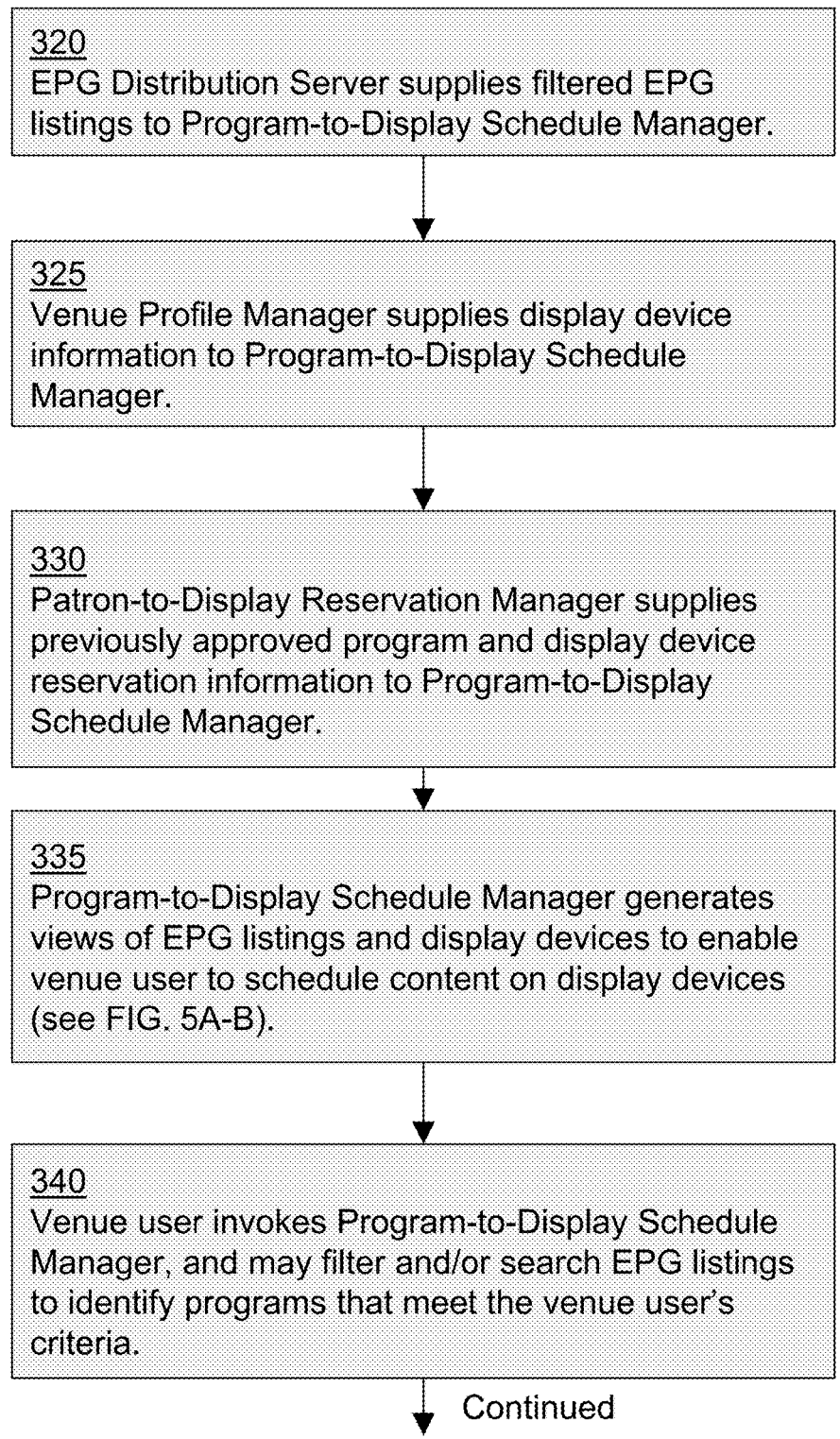

FIG. 2 is a block diagram depicting the Venue Subsystem 150. As shown, the Venue Subsystem 150 can include one or more computing devices typically located at a Venue for providing audio and/or video content to Patrons at the Venue and facilitating the systems and methods for scheduling and controlling the presentation of media content in accordance with one or more of the disclosed embodiments. A Venue can be any public or private space, including businesses, homes, kiosks, gymnasiums, restaurants, bars, clubhouses, airports, stadiums, public gathering places, in which a presentation device is located. Preferably the various devices that comprise the Venue subsystem are networked via one or more data communications networks and one or more of the Venue subsystem components including, preferably, the Widget and/or, are communicatively coupled to at least the system server 105 via the Internet, local or wide area network and the like.

In particular, the Venue subsystem can include one or more Media Sources 155, or be connected to one or more Media Sources via a cable or network, or be capable of receiving content from one or more broadcast Media Sources. Media Sources may provide media content via radio frequency (RF) signals transmitted through coaxial cables or light pulses through fiber-optic cables, or received via radio waves transmitted over the air, or via other means for output by one or more of the presentation devices at the Venue. For example, a Venue may have a satellite telecommunications receiver (for example, a Dish Network or DirecTV satellite dish) or cable telecommunications receiver (for example, a Comcast or Netfinity receiver or integrated receiver and DVR system), telecommunications signal distribution network, one or more matrix switches, one or more signal splitters, one or more coaxial cables, one or more CAT5 or CAT6 cables, one or more Internet modems, one or more routers, one or more audio presentation systems (for example, a stereophonic receiver with associated amplifier and speakers, or a public address systems), one or more visual presentation systems (for example, a television screen, or a video monitor, or a video projector), a local area network (for example, a wired network or WIFI network including requisite signal processing hardware and software).

Also shown is a Widget computing device 160, which comprises one or more hardware and/or software applications operating on a hardware device capable of connecting to the system server 105 over a network (e.g., directly or indirectly via a local/wide area network and/or the Internet), receiving signals from the system server 105, interpreting and processing those signals as necessary, and in turn, generating and communicating appropriate commands directly or indirectly to designated media presentation devices within the Venue and other venue devices such as the Media Management System 170.

The Widget can be a physical device capable of establishing and maintaining a connection to a network, receiving and decrypting an encrypted program change request from the Program Change Manager (further described herein), converting the program change request to a format that can be understood by the Media Management System 170 within the Venue, and communicating the program change request to the Media Management System. The communication to the Media Management System might be in the form of a JSON request, infrared signal, visible wavelength signal, Bluetooth communication, RF signal, audio signal, or other communication protocol.

In some implementations, the Widget could be a desktop computer, laptop computer, tablet computer, mobile phone, Arduino, or other programmable hardware device capable of executing the various functions further described herein. In some implementations, the Widget can be a standalone device specifically provided to the Venue for integration of the existing Venue devices with the system 100. In addition, or alternatively, the Widget can be provided as a software-based virtual control module for executing and operating on an existing computing device at the Venue (e.g., media management system 170) and thereby configuring the existing computing device to implement the various features and functions of the Widget, as further described herein. Alternatively, the Widget may be a physical or virtual device executing and operating outside of the Venue and outside of the Venue's local area network, but interacting with a Venue-side control device, for instance; the Media Management System inside the Venue's local area network.

In operation, for example, the system server 105 may transmit to the Widget a command to tune a specified media presentation device 190, or its controller, to a specified channel on a specified date and at a specified time, in response to which the Widget converts the channel change request (e.g., as received from the Patron-to-Presentation Scheduling and Reservation System) to a format recognizable and understood by the particular media presentation device or its controller, and subsequently transmits the channel change command directly to the media presentation device or its controller (for example, the Widget may issue a JSON request to a media receiver via a WIFI network, causing said media receiver to switch channels, in turn causing a television screen configured to receive media from said media receiver to display video and/or audio content as broadcasted on the channel specified by the channel change request), or indirectly to the media presentation device or its controller (for example, the Widget may issue a TCP/IP command to an infrared signal processor, causing said infrared signal processor to generate an infrared signal which is, in turn, transmitted to a media receiver, causing said media receiver to switch channels, in turn causing a television screen configured to receive media from said media receiver to display video and/or audio content as broadcasted on the channel specified by the channel change request).

Venue Devices 180*a*-180*c* are intended to represent various computing devices and/or data processing apparatuses suitable to facilitate the operation of the Patron-to-Presentation Scheduling and Reservation System, in particular, the Venue-side features and operations. For instance, Venue User Devices can include computing devices operated by Venue staff to set-up and control the particular manner of operation of the system 100 at the Venue. By way of further example, Venue User Devices can also be computing devices (e.g. tablet devices) provided throughout the Venue for the benefit of Patrons thereby enabling the Patrons to interact with the system 100, e.g., in a similar manner to a Patron User Device. Venue Users can access the system 100 via any device that can support a modern web browser and connect to the Internet. Alternatively, Venue Users can access the invention via any device onto which the Venue User can install the Venue App, and which said device is capable of operating the Venue App and connecting to the Internet. Alternatively, Venue Users can access the invention via any device onto which the Venue User can install the Venue Software, and which said device is capable of operating the Venue Software and connecting to the Internet. Venue User Devices can include for example and without limitation, a desktop computer, laptop computer, tablet computer, mobile phone, or other device capable of supporting the operations of either connecting to the Internet, the Venue's LAN or WAN, or of supporting the operations of the Venue App and connecting to the Internet, or of supporting the operations of the Venue Software and connecting to the Internet.

Presentation Device 190 is intended to represent any device capable of presenting visual and/or audio content such as televisions, speaker systems, and other such media output devices (also referred to as a display or audio device). As would be understood by those in the art, a presentation device can include an output device for the display of visual or audio information. Said devices may include one or more signal amplifiers and/or signal processors, visual screens or audio speakers. It can be appreciated that presentation devices can be coupled to various media sources 155 directly or indirectly via media management system 170 and can include various associated controller devices that are not networked.

The Media Management System 170 can be any configuration of hardware, software and networking components necessary to control the selection and presentation of a video and/or audio signal on a display or audio device. Common elements might include a set top box, a matrix switch, or other media management device that controls the content presented on the display or audio device as would be understood by those in the art.

Further Description of the System Server 105

As shown in FIG. 1, the system server 105 is arranged with various hardware and software components that serve to enable operation of the system for scheduling and controlling the presentation of media content 100, including a processor 110, a memory 120, storage 135 and a communication interface 150. The processor 110 serves to execute software instructions that can be loaded into the memory 120. The processor 110 can be a number of processors, a multi-processor core, or some other type of processor, depending on the particular implementation.

A communication interface 150 is also operatively connected to the processor 110 and can be any interface that enables communication between the system server 105 and external devices, machines and/or elements. Preferably, the communication interface 150 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting system server 105 to other computing devices and/or communication networks, such as private networks and the Internet. Such connections can include a wired connection or a wireless connection (e.g., using the IEEE 802.11 standard) though it should be understood that communication interface 150 can be practically any interface that enables communication to/from the system server 105. It should be understood that any of the remote computing devices depicted in FIG. 1 and Venue subsystem 150 can be in direct communication with one-another or the system server 105, indirect communication with one-another or the system server 105, and/or can be communicatively coordinated with one-another or the system server 105 through a computer network, such as the Internet.

Preferably, the memory 120 and/or the storage 135 are accessible by the processor 110, thereby enabling the processor 110 to receive and execute instructions stored on the memory 120 and/or on the storage 190. The memory 120 can be, for example, a random access memory (RAM) or any other suitable volatile or non-volatile computer readable storage medium. In addition, the memory 120 can be fixed or removable. The storage 190 can take various forms depending on the particular implementation. For example, the storage 190 can contain one or more components or devices such as a hard drive, a flash memory, a rewritable optical disk, a rewritable magnetic tape, or some combination of the above. The storage 190 also can be fixed or removable or remote such as cloud based data storage systems.

Various databases can also be stored on the storage. Such databases can contain and/or maintain various data items and elements that are utilized throughout the various operations of the system 100. It should also be noted that, although database 185 is depicted as being configured locally to system server 105, in certain implementations, database 185 and/or various of the data elements stored therein can be located remotely, such as on a remote device or server (not shown), and connected to system server 105 through a network in a manner known to those of ordinary skill in the art. In addition, it should be noted that other information and/or data relevant to the operation of the present systems and methods can also be stored on the storage 135, as will be discussed in greater detail herein.

The one or more software modules 130 can be encoded in the storage 190 and/or in the memory 120. The software modules 130 can comprise one or more software programs or applications having computer program code or a set of instructions executed in the processor 110 and that configure the processor to perform the various operations for scheduling and controlling the presentation of media content as further described herein. Such computer program code or instructions for carrying out these operations can be written in any combination of one or more programming languages. The program code can execute entirely on the system server 105, partly on the system server 105, as a stand-alone software package, partly on the system server 105 and partly on a remote computer/device such as the Widget (as shown in FIG. 2) or entirely on the remote computers/devices. In the latter scenario, the remote computer systems can be connected to the system server 105 through any type of network, including a local area network (LAN) or a wide area network (WAN), or the connection can be made to the external computer (for example, through the Internet using an Internet Service Provider).

It can also be said that the program code of the software modules 130 and one or more of the non-transitory computer readable storage devices (such as the memory 120 and/or the storage 190) form a computer program product that can be manufactured and/or distributed in accordance with the present disclosure, as is known to those of ordinary skill in the art. It should be understood that in some illustrative embodiments, one or more of the software modules 130 can be downloaded over a network to the storage from another device or system via communication interface 150 for use within the system 100. Although the various "manager" and "server" components depicted in FIG. 1 as software modules 130 and are further described herein as "managers," "modules" or "server" components, it can be appreciated that the features and functionality of such components can, in some configurations, be implemented in software executing on the system server 105. However, in addition or alternatively, one or more of these components can be implemented in one or more computing devices that are independent of the system server 105.

The various modules 130 (e.g., manager and server components) and corresponding database elements of the system server 105 are further described herein with continued reference to FIGS. 1 and 2.

The Profile Manager enables Venues, Patrons, and other related parties, including advertisers, content providers, network providers, third-party entities (e.g. beverage supply companies), to register as users of the system and to enter and maintain information relevant to their use of, involvement with, and/or contractual relationship with the system and/or providers of the system and/or other parties using the system and/or other parties providing products and/or services to or via the system 100. The Profile Manager enables Venues, Patrons and other related parties to specify information relevant to their use of and/or involvement with the system. For example, a Venue might provide information including but not limited to details regarding each presentation device under its control, details regarding each source of program content to which the Venue has access, the physical location of the Venue, the maximum seating and standing capacity of the Venue, details regarding the network infrastructure in use at the Venue, the username and password of each of the Venue's users, the role and access rights of each of the Venue's users, the Venue's preferred content, the Venue's restricted or excluded content, the Venue's operating hours, the Venue's primary and alternate contacts, the Venue's billing and payment information, details regarding the Venue's Point of Sale system(s), details regarding the Venue's seating reservation system(s), the Venue's rules regarding reservations, details regarding the Venue's food and beverage offerings, and other information as necessitated to support the accurate listing, scheduling and reservation of content onto presentation devices.

The EPG Cache Server is programmed to poll, on a periodic basis, the Profile Manager to identify which EPG/IPG content should be requested from the EPG/IPG Provider System 140. Based on the query, the EPG Cache Server submits appropriate EPG/IPG requests to the EPG/IPG Provider, receives EPG/IPG data from the EPG/IPG Provider, and stores the received EPG/IPG data in the EPG/IPG Database. As a result, the EPG Cache Server is configured to tailor the requests to the EPG Provider Database to the specific Venue profiles managed by the Profile manager so as to only request and maintain EPG data that is relevant to the profiles under management.

The EPG/IPG Database stores the EPG/IPG data received from the EPG/IPG Provider, as managed by the EPG Cache Server, and can process, perform calculations, sorting, classification, tagging, filtering, and aggregation of the EPG/IPG data so that Venues can readily digest the data. It can be appreciated that other information that could be necessary to facilitate the interaction with the EPG database and the management of data that is relevant to the various user profiles can also be stored in the EPG/IPG database.

The EPG/IPG Distribution Server is configured to deliver EPG/IPG content to users. The EPG/IPG Distribution Server filters EPG/IPG content based on or derived from details included in user profiles, user location, user-selected filters, user search criteria, and other factors, and delivers segments of the EPG/IPG database to users via their respective remotely located devices on request.

The Content-to-Presentation Schedule Manager supports the scheduling of content onto presentation devices at a Venue for display. Each presentation device is associated with a schedule that supports the assignment of content to time slots. If a presentation device is capable of presenting content from more than source simultaneously (for example a television might be capable of presenting a television program from one source while simultaneously presenting audio content from a separate source), then a separate schedule is provided for each supported source and type of content.

The Content-to-Presentation Schedule Manager configures the processor to combine presentation device details, content source details, Venue network details, Venue content preferences, restrictions and exclusions captured in the Venue Profile, EPG/IPG data from the EPG/IPG Distribution Server, and previously saved Content-to-Presentation Schedule data from the Content-to-Schedule Database and to present Venue users, via a respective user device, with one or more presentation schedules for each presentation device. Moreover, the Content-to-Presentation Schedule Manager, based on user inputs received by the system server 105, enables Venue users to assign content of each supported type from the EPG/IPG listing(s) to each presentation schedule. The Content-to-Presentation Schedule Manager is further configured to alert Venue users as to schedule conflicts and time slots to which no content has been assigned. The Content-to-Presentation Schedule Manager also provides tools for facilitating the assignment of content to presentation device schedules, including filters by content genre (e.g. for television content, genres might include Sports, News, Food, Travel, etc., while for audio content, genres might include talk show, news, country music, soul music, 90's hits, etc.), filters by type(s) (e.g. for television content, types might include standard definition; high definition, ultra-high definition, while for audio content, genres might include stereo, mono, Dolby 5.1, etc.), filter by team name, filter by league name, filter by live or recorded events.

The Content-to-Presentation Schedule Manager also configures the processor 110 of the system server 105 to execute functions for automatically assigning content to presentation devices based on preferences captured in (the Venue Profile, as well as in response to ad hoc requests from Venue users. For example, for assigning video content to presentation devices, a Venue might wish to prioritize one genre over another during specific hours on selected presentation devices, or one sport over another on specific days of the week, or content of longer duration over shorter duration during certain hours, within a specified date range. The Content-to-Presentation Schedule Manager also enables Venue users to partially complete the schedules for the Venue's presentation devices, and provides an 'auto-fill' function that shows the Venue user what the schedule will look like if the presentation devices continue sourcing content from the most recently selected source.

The Content-to-Presentation Schedule Database can be configured to store versions of each Content-to-Presentation Schedule, with timestamps indicating each requested schedule update, each successful schedule update, each automated schedule update, each reservation-driven schedule update, requesting process (e.g. Patron-to-Presentation Reservation Manager, or Content-to-Presentation Schedule Manager), EPG/IPG data, and requesting user information.

The Patron-to-Presentation Reservation Manager configures the processor to receive Patron-to-Presentation Reservation requests submitted by Patrons via the Patron Portal, Patron App and Patron Software. Based on the received input and existing schedule for the Venue, and Venue specific requirements, a reservation can be successfully processed and entered according to prescribed requirements. For example, a reservation can be successfully processed and entered when a Patron requests content for which:

1. the selected Venue has an available media source, and
2. the selected Venue has an available presentation device, and
3. the available media source has the ability to supply the content to the available presentation device, and
4. the requested content does not violate any of the preferences or content restrictions recorded in the Venue's Venue Profile, and
5. the requested content type is supported by the presentation device, and
6. other validations, as may be warranted, are applied and passed. Other validations could include a "reasonableness test", such as a Patron is requesting a reservation at noon in Dallas, and another reservation at 1:00 PM in Tokyo—the distance between the two reservation locations is too big and the time to travel that distance is too small, so both reservations are flagged as questionable, and secondary algorithms are commenced to review requesting Patron's history of honored or broken reservations, other account activity, etc. Patron might be forced to complete a Captcha test to ferret out bots, or a question might be posed to the Patron to verify that Patron really intended these reservations.

The processor executing the Patron-to-Presentation Reservation Manager is further configured to transmit notices or messages to the particular device being used by the Patron so as to display a reservation success or reservation failure indicator to the Patron via the Patron Portal, Patron App, or Patron Software.

More specifically, the Patron-to-Presentation Reservation Manager receives EPG/IPG information from the EPG/IPG distribution server, Venue information from the Venue Profile Manager, Content-to-Presentation Schedule information from the Content-to-Presentation Schedule Manager, Patron information from the Profile Manager, Patron Geolocation information from the Geolocation Manager, advertisements and special offers from the Advertisements and Special Offers Manager, and Patron-to-Presentation information from the Patron-to-Presentation Reservation Database.

The Patron-to-Presentation Reservation Manager delivers filtered EPG/IPG listings, Venue listings, content-to-presentation schedules, content recommendations, reservation confirmations and rejections, Venue-driven reservation cancellations, reservation updates, advertisements and special offers, and food and beverage listings to Patrons via the Patron Portal, Patron App, and Patron Software.

The Patron-to-Presentation Reservation Database can be configured to store versions of each Patron-to-Presentation Reservation, with timestamps indicating each requested reservation, each successful reservation, each requested reservation update, each successful reservation update, an indicator of whether the reservation was honored by the Venue, an indicator of whether the reservation was honored by the Patron, a reservation-schedule-to-presentation-schedule cross-reference to the Content-to-Presentation Schedule Database, and requesting user information. It can be appreciated that other information that could be necessary to facilitate scheduling and management of reservations can be stored on the Patron-to-Presentation Reservation Database.

Description of Venue-Side Features of One or More Exemplary Implementations

FIG. 3A-F are flow diagrams illustrating an exemplary routine 300 for receiving and managing Venue information and providing the Venue with access to EPG/IPG listings and associated tools for scheduling and managing EPG/IPG content presented via the Venue's media devices.

At step 305, the Venue user accesses the Venue Portal, or the Venue Software, or the Venue App, and either registers a new Venue user account, or logs in to the system with a previously registered Venue user account. The Venue user account associates one or more user identifiers with a physical Venue, such as a restaurant. A Venue may have multiple registered Venue users, each with specified account management rights and system access rights.

At step 310, the Venue user begins initial registration by completing a Venue Profile, and said Venue Profile is associated with the Venue account and Venue user identifiers. The Venue Profile allows a Venue user having appropriate account management rights and system access rights to record and maintain information regarding the Venue, including but not limited to details regarding each of its plurality of presentation devices under its control (e.g. audio device, video device, audio and video device, Standard Definition video (SD), High Definition video (HD), Ultra HD video (4 k), etc.), details regarding dependencies between presentation devices (e.g. two presentation devices are linked to the same media content source, and will always present the same media content from that source), details regarding dependencies between presentation devices and media content sources (e.g., whether a presentation device is connected, directly or indirectly, to a media content source), and between presentation devices details regarding the provider(s) of media content to which the Venue has access, details regarding each of its plurality of media content subscriptions to which the Venue has a current subscription, the physical location of the Venue, the maximum seating and standing capacity of the Venue, details regarding the network infrastructure in use at the Venue, the username and password of each of the Venue's plurality of users, the role and access rights of each of the Venue's plurality of users, the Venue's preferred content, the Venue's restricted or excluded content, the Venue's operating hours, the Venue's primary and alternate contacts, the Venue's billing and payment information, details regarding the Venue's Point of Sale system(s), details regarding the Venue's seating reservation system(s), the Venue's Patron-to-Presentation Reservation Arrival Time and Check-In Rules, the Venue's Patron-to-Presentation Reservation cancellation rules, Media Content Start Time Rules, Venue's Media Content End Time Rules, Venue's Media Content Interruption Rules, details regarding the Venue's food and beverage offerings, the unique Widget identifier associated with each Widget configured within the Venue's network, and other information as necessitated to support the accurate listing, scheduling and reservation of content onto presentation devices.

The Venue Profile includes information capture and management functions that allow a Venue user having appropriate account management rights and system access rights to describe the Venue's network topology, including which Presentation Devices are connected to which Media Sources, the nature of those network connections, the type, brand and model of each Media Source, network switch, Presentation Device, network management system, content management system, and any software or middleware used in or by the Venue network.

Information captured in the Venue Profile can also be used to support Patron user's efforts to select a Venue for the Patron's visit. For instance, a Patron user may search for a Venue located within a specified zip code, or having HD television screens, or offering a Patron user's preferred beverage.

Preferably, the system server maintains an updated list of media content programming that is available for presentation at the Venue. Accordingly, at step 315, the EPG/IPG Cache Server can be configured to submit an EPG/IPG request to the EPG Provider to query the EPG/IPG Provider for programming information. It can be appreciated that the query can be submitted to the EPG/IPG provider on a periodic basis, on a scheduled basis and/or in response to a request by a Venue user or Patron user. The query can request the entirety of EPG/IPG programming information for a geographic area, or specify subsets of the available EPG/IPG programming information, such as a specific genre, zip code, content provider, etc. The EPG data can be stored in the EPG Database.

Having a completed Venue Profile, a Venue user with appropriate account management and access rights may then invoke the Content-to-Presentation Schedule Manager. It can be appreciated that steps 320-335, further describe the various steps performed by the system server 105 to compile the data necessary to present the schedule managing interface, e.g., Listing view, to the Venue User. Then as further described herein, the Content-to-Presentation Schedule Manager, allows the Venue user to assign media content to presentation devices, thereby creating a schedule of media content to be presented on each of its plurality of presentation devices and further allows the Venue user to assign media content to presentation devices, thereby creating a schedule of media content to be presented on each of its plurality of presentation devices.

The GUI presented to the Venue User showing the Listing View or Device View can be similar to the exemplary screen-shots shown in FIGS. 5A and 5B and described in relation to the Patron user Listing and Device views, as further described below.

In one exemplary implementation, at step 340, in the Listing View provided by the Content-to-Presentation Schedule Manager, the Venue user is presented with a variety of methods for filtering the EPG/IPG listing, e.g. by genre, sport, team, league, HD video, programs currently in progress, channel number or identifier, live events only, date, etc. The Venue user may also search for EPG/IPG programs by program name. If EPG/IPG programs are grouped into channels, the EPG/IPG listing is segregated into channels by column, with each channel's EPG/IPG content presented in an individual column, with the channel identifier and call sign indicated at the top of the column. Content that meets the Venue user's filter and/or search criteria is presented in the columns under its respective channel. Content that does not meet the Venue user's filter and/or search criteria is hidden from view. Channels that contain no content meeting the Venue user's filter and/or search criteria are hidden from view, i.e. the associated column for the channel is hidden in its entirety.

As noted above, the Venue Profile includes information concerning the various presentation devices at the Venue that are useable to display content. Accordingly, through the Listing View, the Content-to-Presentation Schedule Manager can present the Venue user with a listing of the presentation devices at the Venue. Through the listing view, at step 350, the presentation devices can be selected by the Venue user individually to enable assignment of EPG/IPG programs to said presentation device and review the programs assigned to said presentation device. For instance, selection of a particular presentation device can prompt the Content-to-presentation Schedule Manager to provide the Venue user with a schedule of EPG/IPG content to be presented in chronological order via the presentation device, in accordance with the EPG/IPG schedule, e.g., a 1-hour EPG/IPG program beginning at 1:00 PM and ending at 2:00 PM may be followed by another program beginning at 2:00 PM.

In some implementations, via the Listing View, the Content-to-Presentation Schedule Manager can allow the Venue user to assign EPG/IPG programs to a presentation device such that, due to the nature and timing of the EPG/IPG programs, EPG/IPG programs may overlap other EPG/IPG programs, creating an intersection of EPG/IPG programs, also referred to as a schedule conflict. Accordingly, as shown in step 365 of FIG. 3D, the Content-to-Presentation Schedule Manager can be configured to identify such conflicts. Moreover, at step 350 (as shown in FIG. 3C, the Content-to-Presentation Schedule Manager can be configured to, via the Listing View, allow the Venue user to indicate which of the EPG/IPG programs involved in the conflict has priority over the other EPG/IPG program(s) in the conflict, which said priority determines which EPG/IPG program is presented on the presentation device and which EPG/IPG program(s) are interrupted to allow presentation of the priority EPG/IPG program. An individual EPG/IPG program can be in conflict with multiple other EPG/IPG program assignments, and an individual EPG/IPG program can be assigned a different priority for each conflict. For example, an EPG/IPG program (A) that begins at 10:00 AM and ends at 4:00 PM may be assigned to a presentation device. Another EPG/IPG program (B) that begins at 11:00 AM and ends at 12:00 PM may be assigned to the same presentation device, creating a conflict if both EPG/IPG programs A and B cannot be presented by the same presentation device concurrently. The Venue user may assign a higher priority to EPG/IPG program B, thereby allowing EPG/IPG program B to interrupt EPG/IPG program A. When EPG/IPG program B ends at 12:00 PM, EPG/IPG program A resumes. Yet another EPG/IPG program (C) that begins at 3:30 PM and ends at 5:00 PM may be assigned to the same presentation device, creating another conflict if both EPG/IPG programs A and C cannot be presented by the same presentation device concurrently. The Venue user may assign a higher priority to EPG/IPG program A, thereby allowing EPG/IPG program A to continue to its end time, at which point EPG/IPG program C begins, already in progress.

Using the Listing View supported by the Content-to-Presentation Schedule Manager, the Venue user can also select a presentation device to which the Venue user wishes to assign EPG/IPG programs. The Content-to-Presentation Schedule Manager can be configured to respond to such a selection by presenting EPG/IPG programs that can be assigned to the presentation device. The list of EPG/IPG programs that can be assigned to a presentation device is dependent on several factors, including the availability of media source(s), connection(s) between the media source(s) and the presentation device, and media type. Accordingly, the Content-to-Presentation Schedule Manager retrieves the EPG/IPG listing from the EPG/IPG Distribution Server which, in turn, queries the EPG/IPG Database to identify, based on the aforementioned factors, which EPG/IPG programs are available to be assigned to the selected presentation device.

After selecting a presentation device (e.g. a video media presentation screen) for scheduling, the Venue user may subsequently select (e.g., double-click on) an individual EPG/IPG program, as presented by a labeled box in the schedule, thereby assigning the EPG/IPG program to the selected device. If multiple presentation devices are arranged in a group such that they are dependent on each other, i.e. all presentation devices in the group receive media content from the same input device, and will present the same media content, then if a Venue user assigns an EPG/IPG program to one of the devices in the group, the Content-to-Presentation Schedule Manager can be configured to assigns the same media content to all devices in the group, as defined in the Venue Profile.

In some implementations, the Content-to-Presentation Schedule Manager is configured to provide Venue users an option to assign EPG/IPG programs to only a portion of a presentation device's operating schedule, thereby leaving some periods of time in the presentation device's Content-to-Presentation Schedule that have no EPG/IPG programs assigned, or empty. In order to ensure the Content-to-Presentation Schedule for a device does not remain empty for any periods during the Venue's operating hours, at step 355, the Content-to-Presentation Schedule Manager uses one or more of a plurality of rules for populating empty portions of a presentation device's Content-to-Presentation Schedule. One rule may be to continue presenting EPG/IPG programs from the same content source and channel as the previous EPG/IPG program assigned to the presentation device. For example, if a Venue user assigns to a presentation device P1 an EPG/IPG program E1 from Media Source M1, Channel C1 for the period 10:00 AM to 11:00 AM, and the period from 11:00 AM to 11:30 AM is not assigned any EPG/IPG program, the Content-to-Presentation Schedule Manager can automatically attempt to assign an EPG/IPG program E2 from Media Source M1, Channel C1 for the period 11:00 AM to 11:30 AM. This would be the equivalent to turning on a television P1, and tuning its media source M1 to channel C1 at 10:00 AM, at which time the television P1 would present EPG/IPG program E1 from Media Source M1, Channel C1 for the period 10:00 AM to 11:00 AM, after which, assuming no change is made to the Media Source, Channel or Presentation Device, the television P1 would present whatever EPG/IPG program was scheduled to appear on Media Source M1, Channel C1 beginning at 11:00 AM. If the media type is incompatible with the presentation device, or the EPG/IPG program does not pass the content and/or preferences validations defined in the Venue Profile, or if there is no EPG/IPG content available on Media Source M1, Channel C1 immediately following the conclusion of EPG/IPG program E1, then the Content-to-Presentation Schedule Manager can be configured to attempt to assign One or more EPG/IPG programs from a pre-defined Channel C2 from the Media Source M1. If the media type of the EPG/IPG program available on the pre-defined Channel C2 from the Media Source M1 is incompatible with the presentation device, or the EPG/IPG program does not pass the content and/or preferences validations defined in the Venue Profile, or if there is no EPG/IPG content available on Media Source M1, Channel C2 immediately following the conclusion of EPG/IPG program E1, then the Content-to-Presentation Schedule Manager can be configured to attempt to assign one or more EPG/IPG programs from another Channel C3 . . . CN from Media Source M1. The Content-to-Presentation Schedule Manager can be configured to use additional and/or alternative rules, such as preferred genre, preferred source, "attempt to have this presentation device present the same EPG/IPG program as currently being presented on a specified presentation device", etc.

The auto-fill/Preview function of the Content-to-Presentation Schedule Manager can be invoked by the Venue user in both the Listing View (to preview which EPG/IPG programs the Content-to-Presentation Schedule Manager can automatically assign to an individual presentation device) and the Device View (to preview which EPG/IPG programs the Content-to-Presentation Schedule Manager can automatically assign to the plurality of individual presentation devices.). EPG/IPG programs assigned to Content-to-Presentation Schedules automatically by the Content-to-Presentation Schedule Manager can be assigned a visual appearance (color, shading, or other indicator) different from EPG/IPG programs assigned to Content-to-Presentation Schedules by Venue users, and different still from EPG/IPG programs assigned to Content-to-Presentation Schedules by Patron users via the Patron-to-Content Reservation Manager.

Description of Patron-Facing Features of One or More Exemplary Implementations

Turning now to FIG. 4A, which is a high level diagram illustrating a routine 400 for allowing Patron users to create a Patron profile, and for processing Patron user inputs to the Patron-to-Presentation Reservation Manager to search for content and Venues, and for processing a Patron user submitted content reservations.

At step 405, the Patron user accesses the Patron Portal, or the Patron Software, or the Patron App, and either registers a new Patron user account, or logs in to the system (i.e., accesses system server 105) with a previously registered Patron user account. The Patron user account associates a user identifier with a person. A Patron user account is granted a specified set of account management rights and system access rights, with such rights subject to change depending on the configuration of, and functionality provided by the system. The Patron profile manager can track user activity with the system 100 and can be configured to receive information concerning the Patron's purchasing/activity at the Venue from one or more computing systems that record such activity-related information (e.g., venue or third-party reservation systems or rewards programs) and can be configured to automatically adjust Patron rights accordingly as a function of predefined rules. As such, Patron users may gain or lose specified functionality and/or system access rights based on the user's use of the system, earned and/or purchased access agreements, special offers and/or incentives, points and/or loyalty programs, etc. Such automatic rights and incentives management through integration with The Patron user completes a Patron Profile, and said Patron Profile is associated with the Patron account and Patron user identifier. The Patron Profile allows a Patron user having appropriate account management rights and system access rights to record and maintain information regarding the Patron, including but not limited to details regarding each of the Patron's plurality of interests, including the Patron's preferred content genres, preferred sports, preferred leagues, preferred teams, preferred Venues, preferred beverages, preferred foods, preferred smoking or non-smoking Venues, preferred smoking or non-smoking seating within Venues, Patron address and/or zip code.

Having a completed Patron Profile, a Patron user with appropriate account management and system access rights may invoke the Patron-to-Presentation Reservation Manager, which is configured to allow the Patron user to search for EPG/IPG content, at step 410, and ultimately complete and submit a reservation request to enjoy media content at a specified Venue, as further described herein.

For instance the various Patron-to-Presentation Reservation Manager functions can presented to a Patron via the Patron device. For example and without limitation Venue selection functions can include: Select Venue from map based on Zip code or user's geolocation; Search for Venue by name; Select Venue name from dropdown list, filtered by user's geolocation or user-provided zip code; Show preferred Venues saved in Patron Profile; Search for Venue by beverage based on Venues' list of beverages and Patron user's selection of beverage; Search for Venue by beverage based on Venues' list of beverages and Patron user's preferred beverages saved in Patron Profile.

For example and without limitation, results of a Venue search can be presented by the Patron-to-Presentation Reservation Manager to the user via the user device in a list, map or other such visual arrangement. Moreover, the Patron can, through the Patron device, retrieve detailed Venue information from the system server 105, including, without limitation: images of venue, menu, operating hours, details regarding presentation devices, details regarding media sources, subscription packages, details regarding venue's reservation rules, details regarding special offers at venue, and the like.

In addition, the Patron-to-Presentation Reservation Manager can, via the Patron app/portal, provide an option for the Patron user to invoke Reservation creation function for the particular Venue or can view a schedule/grid relating to the availability at the Venue(s).

Moreover, at step 415, the Patron-to-Presentation Reservation Manager via the Patron app/portal can also provide additional search functions such that the user can also search, view or filter the Venues according to parameters relating to content and the presentation of content at prospective Venues. For example the Search by Content according to parameters including: Type (e.g. video or audio, video with audio broadcast by Venue's device, video with streaming audio available to Patron user's device), genre, sport, team name, league name, live content only, HD content only, new content only (not repeats), on now, by channel identifier or number, by program title, or by date. Results can be displayed by the Patron-to-Presentation Reservation Manager through the Patron device. For instance the results can be visually displayed as a schedule/grid showing EPG/IPG results that meet the Patron user's criteria, a schedule/grid showing Venues that have the capacity to present EPG/IPG results that meet the Patron user's criteria and/or a map showing Venues that have the capacity to present EPG/IPG results that meet the Patron user's criteria.

Upon selection of a particular venue, the Patron-to-Presentation Reservation Manager can retrieve information from the particular Venue Profile for presentation to the Patron through the Patron device. The presentation can include information concerning the various presentation devices and content scheduled for display at the Venue through a Listing View and Device View user interface. The information and mariner of presentation while in these views can be similar to the corresponding Listing and Device Views provided to a Venue User by the Content-to-Presentation Schedule Manager as described above. An exemplary GUI presented to the Patron. User via the Patron User device (or a Venue User device) showing an exemplary Listing View and Device View are shown in FIGS. 5A and 5B, respectively.

Various exemplary processes relating to how the Patron-to-Presentation Reservation Manager interacts with the Content-to-Presentation Schedule Manager to process and modify the presentation schedule according Patron requests are further described herein and in relation to FIG. 4B. At step 320, a Patron-to-Presentation Reservation request submitted by a Patron user via the Patron Portal, Patron Software, or Patron App, is received by the Patron-to-Presentation Reservation Manager.

Then at step 425, the Patron-to-Presentation Reservation Manager interacts with the Content-to-Presentation Schedule Manager by communicating a Patron-to-Presentation Reservation request submitted by a Patron user via the Patron Portal, Patron Software, or Patron App, and receiving from the Content-to-Presentation Schedule Manager a response indicating either the reservation was automatically accepted, is pending acceptance via manual intervention by a Venue user, or the reservation was rejected. While the Patron-to-Presentation Reservation Manager is configured to only allow the creation of Reservation Requests that can be honored by the Venue, due to the fact that multiple Patrons might create and submit Reservation Requests to the same Venue within a relatively short span of time, it is possible that a Venue was willing and able to present the requested content at the time the Patron user began the Reservation Request, but unwilling or unable to honor the request by the time the Reservation Request was received by the Content-to-Presentation Schedule Manager.

In some implementations, EPG/IPG programs assigned to the Content-to-Presentation Schedule are assigned one of multiple priority levels, for example and without limitation 3 priority levels described herein.

Priority 1: can include Programs that are scheduled by the Venue, and are effectively locked into the schedule. For example, a Venue makes publicly known their plans to present a specific sporting event on a large format projection screen at the Venue. The media content related to the sporting event, and the presentation device on which the media content will be presented are "locked" in the schedule, and cannot be overridden by a Patron's media presentation requests unless a properly authorized Venue user specifically approves the Patron's media presentation request. Only a properly authorized Venue user can update a locked program assignment, or assign new programming that supersedes a locked program assignment. Programs that are included in a Venue's Content-to-Presentation Schedule as a result of accepted Patron-to-Presentation Reservations are also assigned priority 1 status. Note that multiple Patrons may submit, and have accepted by Venue users, Patron-to-Presentation Reservations for the same program on the same device. Venues have the ability to lock specified devices, either completely, or for portions of specified days of the week, thereby precluding Reservation Requests from being created for specified devices during specified times and dates. Additionally, Venues might want to lock all televisions for busy times like Sunday afternoons during football season, and only accept reservation requests from users who are in the Venue. In other words, a time slot might be locked to Patrons outside the Venue, but unlocked for Patrons who are checked in at the Venue. This is the equivalent of first-come, first-served seating, but with an additional feature that allows Patrons who are present in the physical Venue to request changes to scheduled or currently presented content. Venue management could manually accept or reject the reservation request based on their assessment of the requested content and other Patron interests. The system allows the Patron to select media content and create a request to assign the media content to a presentation device. If Venue management accepts/approves the request, the assignment happens immediately. For content that is currently being aired, the assignment of the content to the schedule causes the Widget to issue the necessary media source tuning instructions and/or network routing instructions and/or presentation device input configuration instructions such that the content is immediately presented on the specified presentation device. For content that will not be available until the future, the content is assigned to the schedule and, at the media content start time, the schedule causes the Widget to issue the necessary media source tuning instructions and/or network routing instructions and/or presentation device input configuration instructions such that the content is immediately presented on the specified presentation device.

Priority 2: can include programs that are scheduled by the Venue, but which the Venue will allow to be changed if Patrons reserve other content. These programs, though they appear on the media presentation schedule, are deemed to be "unlocked", and can be overridden by an approved Patron's media presentation request. Note that an unlocked program can become a reserved/locked program if either (a) a Patron creates a reservation to watch the program, or (b) the Venue updates the schedule to indicate the program is locked. The Venue might lock a previously unlocked program if a Patron starts watching a program, or the Venue determines that the content should be locked due to an expectation that Patrons will want to watch the program.

Priority 3: can include programs that are assigned to the schedule by the Preview function, i.e. programs that result from the Venue leaving a period of time empty in a presentation device's media presentation schedule. These media presentation schedule slots and associated programs are deemed to be "free".

Accordingly, when a Patron user submits a media presentation reservation request, the Scheduler can be configured to attempt to satisfy the media presentation request starting with free schedule slots, then proceeding to unlocked schedule slots, and finally to locked slots. Various processes can be performed to determine to which device a Patron's media presentation reservation request should be assigned, or in which order, if multiple devices are capable of accepting a Patron's media presentation reservation request. In some implementations, the system server 105 can be configured to allow the Patron to decide, or Venues to define the assignment order in the Patron Profile or Venue Profile. By way of further example, a Patron user can be provided with a reduced functionality version of the Venue Scheduler. Frequent Patrons may have preferences of enjoying content on a specific presentation device. Additionally, the Venue details provided through the Patron portal for example, can provide a 3D rendering of the Venue, thereby further enabling Patron users to get a preview of their table location relative to a device location, thereby facilitation the Patron's selection of an appropriate table accordingly.

In some implementations, the scheduler is configured such that a Patron's media presentation reservation request will not supersede a locked program. It is worth noting that a Patron reservation can, in some implementations, create a locked program. If a Patron reservation request can only be partially satisfied, i.e. some portion or portions of the requested program will be superseded by locked programs, the scheduler can communicate the anticipated interruption(s) to the Patron user, e.g. "Attention: This Venue will gladly accept and honor your requested reservation, but your requested program cannot be shown in its entirety at this Venue. Please see the conflicts indicated below, and indicate whether you wish to accept the conflicts and confirm your reservation, or reject the conflicts and create another reservation." The Patron is shown the conflicts, and can be prompted to make a decision and provide a corresponding input. Various other methods for communicating information relating to media presentation schedule conflicts can be implemented.

In some implementations, the Patron can be provided with a Patron-to-Presentation Reservation Check-In Agreement, for example, via the Patron device. The Patron-to-Presentation Reservation Check-In Agreement is an agreement between the Venue and Patron whereby the Venue agrees to present the EPG/IPG content specified in Patron-to-Presentation Reservation if the Patron arrives and checks in at the Venue at or before an agreed upon time, The Venue's default Patron-to-Presentation Reservation Check-In Rules are recorded and managed in the Venue Profile: The Venue's default Patron-to-Presentation Reservation Check-In Rules are incorporated into Patron-to-Presentation Reservations made with the Venue, and are presented to the Patron user at the time the Patron user creates the Patron-to-Presentation Reservation Request. In the Venue Profile, the Venue user specifies the default Check-in rules, such as "Patron must Check-In 10 minutes before content presentation begins", or "Patron may Check-In up to 15 minutes after content presentation begins". If the Patron does not Check-In in accordance with the Patron-to-Presentation Reservation Check-In Agreement, the Venue has the option to cancel the Patron-to-Presentation Reservation, releasing the Presentation Device and/or the Media Source to be used to satisfy other media requests. For instance, the Venue may agree to begin presenting the requested EPG/IPG content on time; and to continue to present the requested EPG/IPG content for a pre-agreed period of time (e.g. 10 minutes) even if the Patron has not yet arrived, after which the Venue reserves the right to cancel the reservation if the Patron has not yet performed the agreed upon Check-In process at the Venue.

Because the Patron user may request to enjoy only the latter portion of an EPG/IPG program, for instance, a Patron user may only be interested in watching the last two hours of an eight-hour golf match, or the Patron user may know in advance that the Patron user will not be able to arrive at the Venue until 45 minutes after the start of a two-hour program. The Patron-to-Presentation Reservation Request allows the Patron user to indicate a preferred Media Content Start Time. The Venue's Media Content Start Time Rules captured in the Venue Profile determines the Media Content Start Time values allowed by the Patron-to-Presentation Reservation Request. For instance, the Venue's Media Content Start Time Rules may only allow content presentation to be scheduled to begin on the hour and half hour, unless the program's actual start time is specified in the EPG/IPG as starting at a time other than on the hour or half hour, in which case the Venue's Media Content Start Time Rules may allow the Media Content Start Time value to be set to the actual start time, or to a value on the hour or half hour during the course of the program. Additionally, the Media Content Start Time Rules may allow Patron users to request media content that conflicts with previously scheduled media content. For instance, a Patron user may request media content that begins at 2:00 PM and continues until 4:00 PM. If a previously scheduled program were in conflict with the requested media content such that the requested media content could not begin being presented until 2:30 PM, the Venue's Media Content Start Time Rules may be configured to allow or disallow the Patron user to create a Patron-to-Presentation Reservation Request for the requested content. The allowed values for the Media Content Start Time might then be either 2:30 PM, 3:00 PM, or 3:30 PM. The Patron-to-Presentation Reservation Request allows the Patron user to indicate acceptance of specified interruptions of the requested media content.

Similarly, the Patron user may request to enjoy only the former portion of an EPG/IPG program. For instance, a Patron user may only be interested in watching the first two hours of a four-hour bike race, or the Patron user may know in advance that the Patron user will be leaving the Venue at a specified time, which time precedes the requested media content end time. The Patron-to-Presentation Reservation Request allows the Patron user to indicate a preferred Media Content End Time. The Venue's Media Content End Time Rules captured in the Venue Profile determines the Media Content End Time values allowed by the Patron-to-Presentation Reservation Request. For instance, the Venue's Media Content End Time Rules may only allow content presentation to be scheduled to end on the hour and half hour, unless the program's actual end time is specified in the EPG/IPG as ending at a time other than on the hour or half hour, in which case the Venue's Media Content End Time Rules may allow the Media Content End Time value to be set to the actual end time, or to a value on the hour or half hour during the course of the program. Additionally, the Media Content End Time Rules may allow Patron users to request media content that conflicts with previously scheduled media content. For instance, a Patron user may request media content that begins at 2:00 PM and continues until 4:00 PM. If a previously scheduled program were in conflict with the requested media content such that the requested media content could not be presented in its entirety due to a previously scheduled program beginning at 3:30 PM, the Venue's Media Content End Time Rules may be configured to allow or disallow the Patron user to create a Patron-to-Presentation Reservation Request for the requested content. The allowed values for the Media Content End Time might then be either 2:30 PM, 3:00 PM, or 3:30 PM. The Patron-to-Presentation Reservation Request allows the Patron user to indicate acceptance of specified interruptions of the requested media content.

Similarly, the Patron user may request to enjoy only several portions of an EPG/IPG program. For instance, a Patron user may only be interested in watching the first two hours, and the last two hours of an eight-hour golf match, or the Patron user may know in advance that the Patron user will be leaving the Venue at a specified time during the program, but will be returning before the conclusion of the program. The Venue's Media Content Interruption Rules captured in the Venue Profile determines the Media Content Interruption values allowed by the Patron-to-Presentation Reservation Request. For instance, the Venue's Media Content Interruption Rules may only allow content presentation to be scheduled to be interrupted once, and such interruptions may be scheduled to occur only on the hour and half hour, and have durations of a maximum and minimum number of minutes, and be specified to have a duration divisible by 30 minutes. Additionally, the Media Content Interruption Rules may allow Patron users to request media content that conflicts with previously scheduled media content. For instance, a Patron user may request media content that begins at 1:00 PM and continues until 7:00 PM. If a previously scheduled program were in conflict with the requested media content such that the requested media content could not be presented in its entirety due to a previously scheduled program beginning at 3:00 PM and ending at 4:00 PM the Venue's Media Content Interruption Rules may be configured to allow or disallow the Patron user to create a Patron-to-Presentation Reservation Request for the requested content. The Patron-to-Presentation Reservation Request allows the Patron user to indicate acceptance of specified interruptions of the requested media content.

As previously noted, the system 100 can be configured to, at step 430, identify if and when a particular Patron, who has previously submitted a reservation request has honored the representation that they will visit the Venue. Check-In can be performed via one or more of several methods. If the Patron user allows the system to verify the geolocation of the Patron user's device, the system server 105, through the venue app or portal can verify the geolocation of the Patron device at the time of the reservation, for instance, as provided by a GPS or WIFI-based location services. If the geolocation of said device matches the geolocation of the Venue at the Check-In time specified in the Patron-to-Presentation Reservation Check-In Agreement, then the Patron is deemed to have satisfied the Check-In process. Alternatively, a Venue user may update the Reservation in the system to indicate that the Patron is present, thereby deeming that the Patron has satisfied the Check-In process, for instance, the update can be input using a table-reservation system that is in communication with the system server 105 and configured to provide access to such information to the system server. Alternatively, the system server 105 can generate and provide a unique barcode associated with the Patron-to-Presentation Reservation to the user (e.g., via the patron app/portal), allowing the Patron user to present to the Venue's integrated barcode scanner either a printed reservation or a display device that can present in the barcode in scannable form to the Venue's integrated barcode scanner. The system server 105 can be configured to receive inputs from the barcode scanner, and compare the barcode with barcodes associated with the Venue's current Patron-to-Presentation Reservation. Alternatively, the system can be configured to interact with a Bluetooth (or other suitable wireless transceiver) device located in the Venue, whereby a connection is automatically established between the Venue's Bluetooth device and the Patron's device, and the system receives a notification from either or both of the Venue's Bluetooth device or the Patron's device, indicating that the reservation has been honored by the Patron. Alternatively, the Widget can be configured to detect when the Patron's device has logged onto or made direct contact with the venues WIFI network, and the system then receives a notification from either or both of the Widget or the Patron's device, indicating that the reservation has been honored by the Patron. Alternatively, the Patron app can be configured to detect the Venue's WIFI network, and the system then receives a notification from either or both of the Widget or the Patron's device, indicating that the reservation has been honored by the Patron.

To verify that the Venue has honored a reservation, the system server 105 can also be configured to periodically query the Media Source AND/OR matrix switch AND/OR Presentation Device AND/OR intermediary devices AND/OR software/middleware to validate that the EPG/IPG content specified in the Patron-to-Presentation Reservation is being presented in accordance with the Patron-to-Presentation Reservation.

Preferably, the system server also records the results of the Check-In process in storage, indicating whether the Patron satisfied the Patron-to-Presentation Reservation and whether the Venue satisfied the Patron-to-Presentation Reservation. The results of Check-In process can thus be used in separate reliability ratings associated with the Venue and the Patron.

In addition, the Venue Profile can include records and default Patron-to-Presentation Reservation Cancellation Rules. The Venue's Patron-to-Presentation Reservation Cancellation Rules can thus be incorporated into Patron-to-Presentation Reservations made with the Venue, and can be presented to the Patron user at the time the Patron user creates the Patron-to-Presentation Reservation Request.

Scheduling and Control of Content Presentation

Further aspects of one or more of the disclosed embodiments relating to scheduling and actively coordinating the presentation of media content according to the schedule are further described herein with continued reference to the exemplary system 100 described in relation to FIGS. 1 and 2.

As previously noted, the Content-to-Presentation Schedule Manager operating on the system server 105 can be configured to coordinate and monitor the implementation of the Content-to-Presentation Schedules for the Presentation Devices at the Venues supported by the system 100. For example, a Presentation Device (P1) at a Venue (V1) has a Content-to-Presentation Schedule (C1) with EPG/IPG Programs (E1 . . . En) assigned to time slots, with each EPG/IPG Program E1-En having parameters including, for example and without limitation, a beginning time, end time, Media Source identifier, Content Type identifier, EPG/IPG Program identifier, and channel identifier and/or frequency identifier and/or station identifier and/or URL and/or media feed identifier, etc. as appropriate.

Figure 6A:
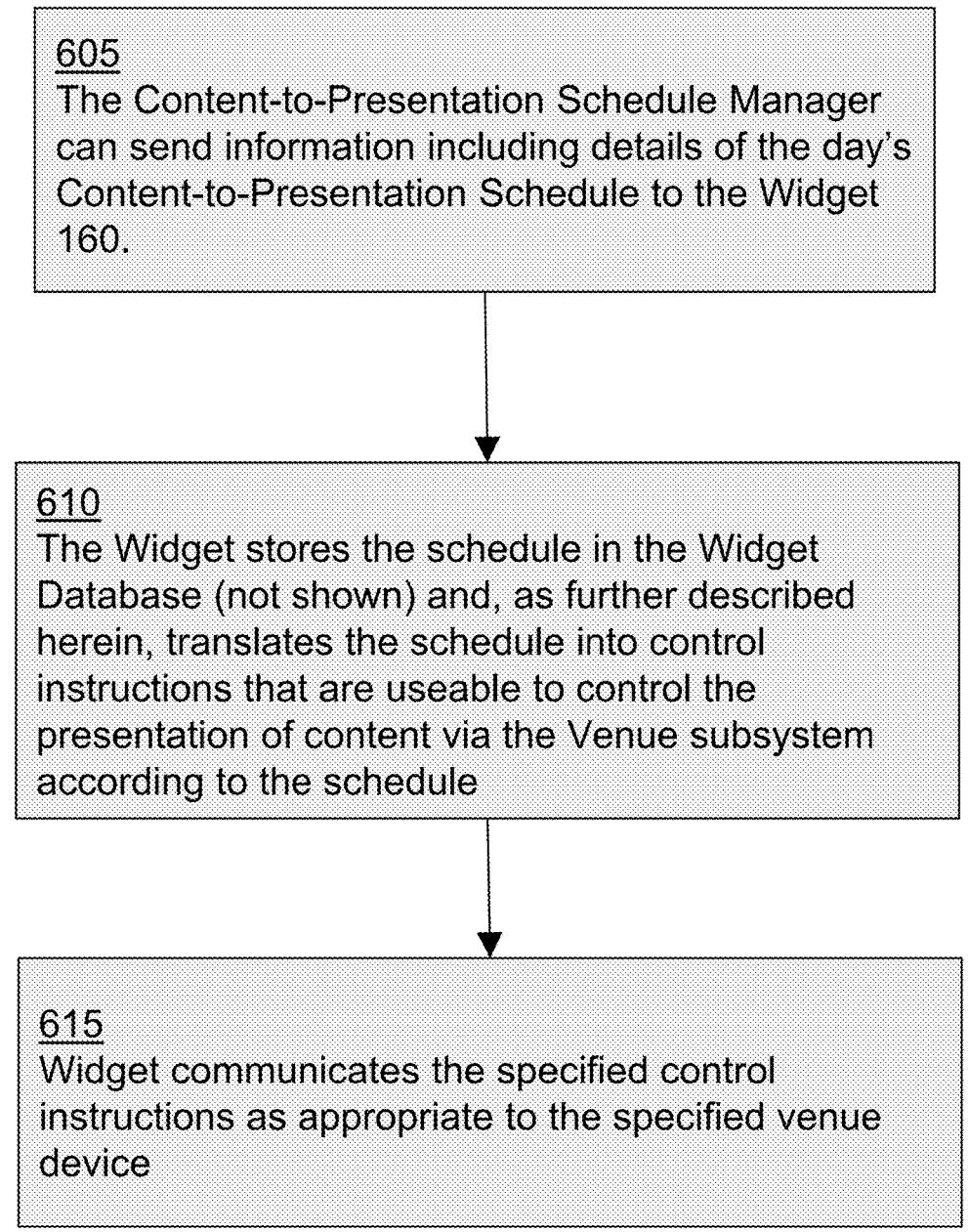

An exemplary routine for actively controlling the display of content at one or more presentation devices according to the Content-to-Presentation Schedules is depicted in FIG. 6 and further described herein. At step 605, periodically, for instance, each day, at a scheduled time configured by the Venue user in the Venue Profile, the Content-to-Presentation Schedule Manager can send information including details of the day's Content-to-Presentation Schedule to the Widget 160. The Widget stores the schedule in storage medium (not shown) and, as further described herein, at step 610, can translate the schedule into control instructions that are useable to control the presentation of content via the Venue subsystem according to the schedule. At step 615, at a time specified for a particular scheduled presentation event, the Widget transmits the control instruction to the appropriate device in the Venue subsystem device to make the necessary device-setting changes to present the scheduled content.

More specifically, the Widget interprets the start time for each EPG/IPG program, and creates a Presentation Device Update Schedule, which specifies the Media Source from which the EPG/IPG program is provided, channel identifier and/or frequency identifier and/or station identifier and/or URL and/or Media feed identifier as appropriate, the Presentation Device(s) to which the EPG/IPG program is to be routed, and the routing instructions. For matrix switch installations, the routing instructions can include the Media Source identifier (or input port, as appropriate) and Presentation Device identifier for each Presentation Device (or output port, as appropriate) to which the EPG/IPG program is scheduled to be routed. At the EPG/IPG program start time, the Widget communicates the specified change of channel identifier and/or frequency identifier and/or station identifier and/or URL and/or media feed identifier as appropriate to the specified Media Source, and communicates the specified change of routing commands to the matrix switch(es).

The Widget can be configured to integrate with various different Media Management System configurations so as to effectively update EPG/IPG programs presented via presentation devices. For instance, if one Presentation Device is connected to a single Media Source (e.g., 155), changing the EPG/IPG program presented on a specified Presentation Device, the Widget performs this action by communicating with the single specified Media Source, and commanding the specified Media Source to change from the current channel, frequency, station, URL, media feed, etc. to another specified channel, frequency, station, URL, media feed, etc. As the specified Presentation Device will present the EPG/IPG content fed by the specified Media Source, it is not necessary to communicate with the specified Presentation Device.

Similarly, if multiple Presentation Devices are connected to one Media Source in a many-to-one relationship, perhaps via a signal splitter, the Widget can be configured to change changing the EPG/IPG program presented on the specified plurality of Presentation Devices connected to a single specified Media Source by communicating with the specified Media Source, and commanding the specified Media Source to change from the current channel, frequency, station, URL, media feed, etc. to another specified channel, frequency, station, URL, media feed, etc. As the plurality of the specified Presentation Devices connected to the specified Media Source will present the EPG/IPG content fed by the specified Media Source, it is not necessary to communicate with the specified Presentation Devices.

If one Presentation Device is connected to more than one Media Source, the Widget can be configured to change the EPG/IPG program presented on a specified Presentation Device by communicating with the specified Media Source, and commanding the specified Media Source to change from the current channel, frequency, station, URL, media feed, etc. to another specified channel, frequency, station, URL, media feed, etc. AND/OR communicating with the specified Presentation Device and commanding the specified Presentation Device to change from its current Media Source to another specified connected Media Source AND/OR communicating with a specified routing switch to command the specified routing switch to route the signal from a specified Media Source to the specified Presentation Device.

If multiple Presentation Devices are connected to multiple Media Sources in a many-to-many relationship, perhaps via a matrix switch, the Content Change Manager can use the network mapping information captured in the Patron Profile to derive the appropriate content change instructions, which may include instructions for a specified Media Source, commanding the specified Media Source to change from the current channel, frequency, station, URL, media feed, etc. to another specified channel, frequency, station, URL, media feed, etc., AND/OR instructions for a specified Presentation Device, commanding the specified Presentation Device to change from its current Media Source to another specified connected Media Source AND/OR instructions for a specified matrix switch, commanding the specified matrix switch to route EPG/IPG content from the specified Media Source to the specified Presentation Device.

An exemplary system initiation/daily startup routine can be as follows:

As an initial step, the Widget creates a socket connection with pubtelly server over the network. Then, the Widget initiates a heartbeat process between the Widget and the pubtelly server to monitor and maintain a connection with the pubtelly server. Upon establishing a reliable connection, the Widget can send a unique Widget Identifier to the server, identifying the Widget to the server. Moreover, the Widget can request initial configuration parameters including, for example and without limitation, media source tuning, switch routing, closed captioning settings (e.g. On/Off, language, closed caption font style, closed caption font size, closed caption location on screen), audio source tuning, audio source selection, audio volume, content management system commands and/or settings, software and/or middleware commands and/or settings, network commands and/or settings, and other presentation device adjustments information from pubtelly server.

In response to the identification and/or request received from the Widget, the pubtelly server, in particular the Content Change Manager uses the Widget Identifier received from the Widget to query the Content-to-Presentation Schedule Manager for initial configuration values associated with the Widget Identifier. Initial configuration values may consist of a device identifier, parameters and/or commands to establish the specified settings necessary to achieve the proper state for the specified device, and an execution time, e.g., a specified Media Source having a specified Internet protocol address or machine identifier is to be tuned to a specific frequency at a specific time.

It can be appreciated that lookup tables ,including settings and control parameters for each of a Venue's media systems (e.g., Media Source(s), network switch(es), Presentation Device(s), network management system(s), content management system(s), and any software or middleware used in or by the Venue network) can be maintained on the pubtelly server. Thus, the Content Change Manager is enabled to generate specific instructions based on the look-up table that can be interpreted and acted upon by each of a Venue's plurality of media systems, and the execution of said instructions resulting in the Venue's media devices having the appropriate and necessary status, such that Media Content is presented by the Venue's Presentation Devices in accordance with the Content-to-Presentation Schedule.

Turning briefly to FIG. 6B, which is another exemplary routine for controlling the presentation devices in accordance with the content presentation schedule. In some embodiments, the system can be configured such that the Content Change Manager can be configured to, at step 630, generate all commands necessary to perform all content changes related to the entirety of the Content-to-Presentation Schedule associated with a specified Widget (i.e., the particular Venue), and subsequently communicate the entirety of those commands to the Widget for storage by the Widget in a database local to the Widget. At step 635, at the time specified with a particular instruction, the Widget can convert the channel change request to a channel change request that is understood by the particular set top box, matrix switch, or other media management device that controls the content presented on the particular display device. In addition or alternatively, one or more of the commands can be relayed by the Widget to the appropriate Venue subsystem device, without conversion.

In some implementations, the Widget can be configured to issue the specified content change commands as appropriate even if the Widget is not able to communicate with the system server. In addition or alternatively, the Content Change Manager can be configured to generate and transmit only a specified portion of those commands, for example, all commands necessary to control the Venue for today, or, by way of further example, real-time commands for immediate or "on the fly" execution.

In some implementations, the system can be configured such that the EPG Distribution Manager sends to the specified Widget the entirety of the existing EPG/IPG relevant to the Venue's media subscriptions, or a portion thereof (for example, the EPG/IPG for today and tomorrow) for storage by the Widget in a database local to the Widget, thereby enabling the Widget to support the ongoing maintenance and monitoring of the Venue's Content-to-Presentation Schedule even if the Widget is not able to communicate with the pubtelly server.

In some implementations, the system can be configured such that the Widget contains or has local access to the lookup tables related to the Venue's media systems that are maintained on the pubtelly server. Thus the Widget can be configured to generate the specific instructions that can be interpreted and acted upon by each of the Venue's plurality of media systems, with the execution of said instructions resulting in the respective devices having the appropriate and necessary status such that Media Content is presented by the Venue's Presentation Devices in accordance with the Content-to-Presentation Schedule. It can be appreciated that the Content-to-Presentation Schedule can be sent to the specified Widget by the pubtelly server, and/or maintained locally by the specified Widget.

In some implementations, the Widget can be configured such that, after receiving from the system server information including but not limited to the Venue Profile; the entirety of the Venue's EPG/IPG or a portion of the Venue's EPG/IPG for a period (for example, the Venue's EPG/IPG for today and tomorrow); the entirety of the Venue's Content-to-Presentation Schedule or a portion of the Venue's Content-to-Presentation Schedule (for example, the Venue's Content-to-Presentation Schedule for today and tomorrow); the lookup tables related to the Venue's media systems, that the Widget could interact directly with the Venue App and/or Venue Software configured on the Venue User Device, thereby enabling the Venue to continue updating a local version of the Content-to-Presentation Schedule and receiving the benefits of the Content Change Manager even if the Widget is not able to communicate with the system server. Moreover, the Widget can be configured to communicate to the system server any updates that have been made in the Venue's offline local Content-to-Presentation Schedule when the Widget is next able to establish a connection with the server. As such, the system server can reconcile the changes in the server-side Content-to-Presentation Schedule and synchronize with the Widget accordingly.

In view of the foregoing exemplary configurations of the system 100, it can be appreciated that various processes for controlling the content that is presented on one or more of the Presentation devices at the Venue can be implemented using the Widget, while other aspects relating to control can be performed/implemented using the server such that control is coordinated by both the Widget 160 and the system server 105. Accordingly, it should be appreciated that one or more of the routines or individual steps described as being handled by the Widget exclusively can, in some configurations, be implemented by the server, and vice versa.

It can also be appreciated that, in some implementations, the Widget can be configured to support some or all of the functions described in relation to the Content-to-Presentation Schedule Manager and/or Content Change Manager and/or EPG/IPG Cache Manager and/or EPG/IPG Distribution Manager, thereby enabling the Venue to continue to receive some portion or all of the functional benefits of the Content-to-Presentation Schedule Manager and/or Content Change Manager and/or EPG/IPG Cache Manager and/or EPG/IPG Distribution Manager, for instance, in the event the Widget is unable to establish or maintain a connection with the pubtelly server. Accordingly, the Widget can be configured to communicate to the server 105 any updates that have been made in the Venue's offline local Content-to-Presentation Schedule when the Widget is next able to establish a connection with the server.

In accordance with one or more of the disclosed embodiments, an exemplary routine performed by the system server 105 and Widget 160 to actively monitor and control presentation of content at the Venue can include one or more of the following steps: First, the Content Change Manager sends configuration values to Widget, either individually or in batch(es), in secure/encrypted form. The Widget receives secure/encrypted configuration values from Content Change Manager, and decrypts configuration values and stores the configuration values in configuration database local to the Widget. At the execution time specified for each command, the Widget communicates commands to specified Media Source(s), network switch(es), Presentation Device(s), network management system(s), content management system(s), as well as any software or middleware used in or by the Venue network. The specified Media Source(s), network switch(es), Presentation Device(s), network management system(s), content management system(s), as well as any software or middleware used in or by the Venue network, respond to commands received from the Widget and adjust their respective operation accordingly. The specified devices can also broadcast message(s) regarding the results of the commands received, either independently or in response to a status query from the Widget. The Widget receives any and all messages broadcast and can be further configured to log the messages in a log database local to the Widget. Moreover, the Widget can also be configured to communicate the logs to Content Change Manager synchronously or asynchronously, individually or in batch(es), as configured. To the extent that the messages report any errors, the Widget can be configured to handle any errors it receives by reissuing commands up to a specified number of attempts, after which the Widget can further inform the server of the reported issue and the Widget continues with the process until complete. At completion of the baseline setting, the Widget sends a message to the pubtelly server indicating completion of the baseline, and requests next channel change/switching/etc. for each device. In some implementations, the Widget can be configured to continue to issue the previously failed commands up to a specified number of retries, and can also be configured to send messages to users or administrators (e.g., a message to the Venue's IT team and to the Patron) alerting the parties to the issue.

Subsequently, the Widget receives the requested information regarding next channel change/switching/etc. for each device and issues instructions to the specified devices accordingly.

In the event that any schedule updates occur that would require updating of the Next channel change/switching/etc. info for any device, switch, or source, then server sends said information to the Widget. Upon receipt of said information the Widget can update the Widget's next change database. If a user (either a Patron or Venue user) enters an immediate change request directly or indirectly into the schedule, the server sends the details of that request as a next update command to the Widget, with a corresponding time for the change, say, immediate. Accordingly, the Widget sends out the commands to the sources, switches, devices, etc. and upon completion, the Widget can again ask for next channel, or an original command from the server might be stored in the next channel database for subsequent processing.

It should be appreciated that in some implementations, the Widget can be an optional element of the proposed solution, and can primarily be used if the system server 105 cannot communicate directly with one or more sources, devices or switches within the Venue subsystem network, for instance, in the case where one or more sources, devices or switches will only respond to commands that are issued by a device located on the local area network. Accordingly, the Widget can be used to overcome this and other such obstacles by being a local relay for commands received from the system server, which resides outside the Venue's LAN.

In accordance with one or more of the exemplary embodiments, the Content Change Manager can be configured to communicate the Content Change Instructions to the Widget. The Widget, in turn, communicates the Content Change Instructions to the specified Media Source AND/OR the specified Presentation Device AND/OR the specified matrix switch. The Widget can be configured to receive any responses, including error messages, confirmation messages, etc. received from the Media Source, Presentation Device, and/or matrix switch, and log the responses. If responses indicate errors, alerts, or delays, the Widget addresses each error, alerts, AND/OR delay response as appropriate.

It can be appreciated that the Widget can be configured with lookup tables containing the various responses that can be received from the Venue's media devices (e.g., Media Source(s), network switch(es), Presentation Device(s), network management system(s), content management system(s), and any software or middleware used in or by the Venue subsystem), and that the Widget can also be configured to perform pre-defined steps to resolve issues specified AND/OR implied in said responses. After comparing said responses received with the configured response lookup tables, the Widget takes predefined steps to resolve issues, overcome delays, AND/OR determine that other intervention processes are necessary to resolve the issue(s) indicated by the response(s) received. Preferably, the Widget is configured to log, in a local or network accessible storage, one or more of the responses received, as well as steps taken by the Widget to resolve said issues, and subsequently logs one or more of the responses received during the processes involved in resolving the reported or implied issues, and continues this process for a predefined amount of time/cycles.

After the Widget performs any issue resolution steps, the Widget can be configured to pass the results of each process to the Content Change Manager for evaluation. Results sent by the Widget to the Content Change Manager may include, but are not limited to, indicators of success, indicators of responses received from the Venue's Media Source(s), network switch(es), Presentation Device(s), network management system(s), content management system(s), and any software or middleware used in or by the Venue network, a log of all processes performed by the Widget, and current status of any and all devices queried AND/OR commanded by the Widget. It can be appreciated that the system can be configured such that the Widget interacts with the Content Change Manager synchronously or asynchronously. Also, it can be appreciated that the system can be configured such that Content Change Commands, activities, and responses are coordinated individually AND/OR in batches.

It should be noted that various media sources, intermediary devices (including matrix switches, splitters, content management devices, middleware, HDMI-to-IP converters, IP-to-HDMI converters, etc.) and presentation devices can be arranged in various ways in a particular Venue subsystem. As a result there are a number of possible ways in which the presentation devices can be controlled. Accordingly, to integrate with the legacy system, the Widget 160, either alone or in combination with the back-end system server 105, is configured to perform the function of translating the presentation control schedule into functional commands that are communicated to and acted upon by the media sources, intermediary devices, and presentation devices within the Venue subsystem/network. In some implementations, the Widget can include an input-to-output mapping module, which is configured to use a lookup table or other predefined rules to translate a particular schedule command into an actionable instruction.

By way of further example, there exist configurations in which multiple media sources are connected to multiple presentation devices via one or more matrix switches. In such a configuration, each presentation device might be configured to present content sourced from one and only one media source at a given time, and each media source might be configured to serve one and only one stream of media content at a given time. Thus, for example, a configuration having twelve media sources and 64 presentation devices is limited to simultaneously allocating up to twelve distinct media content streams to up to 64 presentation devices, with each of those twelve distinct media content streams being presented by as few as zero, and as many as 64 presentation devices, and each presentation device presenting as few as zero, and as many as one simultaneous media content streams.

In such a configuration, it is possible that one or more of the media sources is capable of offering unique media content, that is not available for streaming from the other eleven media sources. It is also possible that some media content is available from more than one of the twelve media sources, i.e. the media content is "common". By example and without limitation, it is possible that at a time T1, a media source S1 is capable of offering unique media content MU and of offering common media content MC, and said media source S1 is at time T1 tuned to provide the common media content MC, and the common media content MC is routed through the matrix switch to be presented on Presentation Device P1. Also at time T1, another media source S2 is capable of offering the common media content MC, and either (a) the matrix switch is configured such that there are no Presentation Devices currently presenting media content from media source S2, or (b) any and all Presentation Devices to which media content from Media Source S2 is being routed are not being enjoyed by any Patrons. In this scenario, media source S2 is considered "free", i.e. the media source S2 can be tuned to present different media content without negatively impacting any Patrons. If at time T1 the system receives a request to present unique media content MU on presentation device P2, and presentation device P1 is expected to continue to present common media content MC, it is possible to tune the free media source S2 to offer the common media content MC, and subsequently route the common media content MC from media source S2 through the matrix switch to be presented on presentation device P1, thereby disconnecting media source S1 from presentation device P1, and making media source S1 "free". Media source S1 can now be tuned to offer unique media content MU, and subsequently the unique media content from media source S1 can be routed through the matrix switch to be presented on presentation device P2.

This process, by which media programs are specified, a source (or sources) for the specified media programs are identified, the multiple media sources are tuned in accordance with specified requirements, and the matrix switch is configured to route media programs in accordance with Patron requests, is complex and cannot be effectively performed manually. In accordance with one or more of the disclosed embodiments, the system (e.g., the system server 105 and/or the Widget 160) can be configured to automatically identify the optimum tuning of media sources based on the EPG/IPG available from each media source, the current tuning of each media source, the current routing of each media source to each presentation device, the current use status of each presentation device (e.g. a television being watched by a Patron is in use, whereas a television that is either turned off or not being watched by a Patron is free), and the possible mapping of each media source to each presentation device as supported by the Venue's network infrastructure. The system can be further configured to, based on the EPG/IPG available from each media source, the current tuning of each media source, the current routing of each media source to each presentation device, the current use status of each presentation device, the possible mapping of each media source to each presentation device as supported by the Venue's network infrastructure, automatically and optimally define the subsequent routing of media sources to presentation devices, and subsequently issue tuning and routing commands to the various media sources, matrix switch(es), content management systems, and/or presentation devices as appropriate, thereby seamlessly controlling the presentation across the various Venue devices in a manner that minimizes disruption of the concurrent Patron and Venue programming requests. Moreover, the automated tuning and routing process drastically reduces human effort and the time delay between the request for content and the presentation of content, and eliminates human error which may result in improperly tuned media source(s) and/or improperly routed media content(s).

The importance of the automated tuning and routing process increases as the number of media sources and presentation devices increases. It is common for a sports bar to have twelve or more media sources and 60 or, more television screens. Identifying, and subsequently implementing the optimum tuning and routing solution to present a Patron's requested media content on one or more presentation devices while all twelve media devices and 64 television screens are in use, and while the sports bar is at capacity with noisy, excited Patrons is not practical, and the re-tuning and. re-routing processes via manual process is far too time consuming to be performed without negatively impacting the presentation of content and thus, the Patrons' media content experience.

The system can be further configured to determine the optimum order in which the media sources can be retuned and the matrix switch routings updated to minimize negative impacts on the presentation of content at the Venue and, thus, the Patrons' media content experience. The mapping of media content to media sources to presentation devices is preferably performed by the system server 105 and/or the Widget 160, which can be configured to determine whether the requested media content can be sourced without interfering with previously scheduled and/or reserved media presentations. If it is determined that the requested media content can be sourced without interfering with previously scheduled and/or reserved media presentations, then the tuning order and routing order is analyzed by the system to determine the optimum order in which to re-tune the various media sources necessary to satisfy the most recent request, and the optimum order in which routing instructions should be updated to minimize negative impacts on the Patrons' media content experience. These processes can be algorithmically determined and implemented by the system, with fine tuning depending on device specifications.

The re-tuning of media sources and re-routing of media sources to presentation devices can be encapsulated into a single series of actions, or into a collection of discrete actions, with said actions being carried out by the system immediately upon request by an authorized user, or queued to occur at a specified time, or queued to occur when an authorized user invokes a command. For example, if the system determines that the re-tuning and re-routing process is expected to have a negative impact on Patrons' media content experience due to the process causing a brief interruption in video and/or audio presentation, the system can queue the re-tuning and re-routing processes and prompt a Venue user to actively initiate, using a Venue device, the processes during a commercial break, or during a lull in the media content. It can also be appreciated that the particular time for executing the processes can be automatically predicted by the system so as to eliminate the need for manual user input or otherwise perform the processes in the event that a command is not received.

It can be appreciated that, based on the configuration of the Venue subsystem and the particular combination of presentation devices, control devices and routing devices, alternative instruction mapping solutions can be implemented by the widget and server to control the operation of the devices in accordance with the presentation schedule.

According to a further aspect of one or more of the disclosed embodiments, the system can be configured to automatically provide, on behalf of third party goods and service providers, incentives to Patrons. For instance, a Venue, Television Network, Television Channel, Cable Network, Satellite Network, Radio Network, Sports Team, Sports League; content producer, beverage producer, food producer, food distributor, beverage distributor, advertiser, etc. may wish to entice Patrons to experience specified media content. These parties may use the system to communicate and/or recommend the availability, nature, scope, timing, location, cost, benefits, and/or other facets of specified media content to Patrons via the Patron App, Patron Software, and/or Patron Portal. These parties may create alerts and/or reminders in the system, and system can be configured to communicate said alerts and/or reminders to Patron via one or more of several methods allowed by the Patron App, Patron Software, and/or Patron Portal, including but not limited to emails, text messages, pop-up notifications, sounds, vibrations, messages delivered within or through the Patron App, Patron Software, and/or Patron Portal.

Similarly, a Venue, Television Network, Television Channel, Cable Network, Satellite Network, Radio Network, Sports Team, Sports League, content producer, beverage producer, food producer, food distributor, beverage distributor, advertiser, etc. may wish to entice Patrons to purchase and/or otherwise consume specified products and/or services. These parties may use the system to communicate and/or recommend the availability, nature, scope, timing, location, cost, benefits, and/or other facets of specified products and/or services to Patrons via the Patron App, Patron Software, and/or Patron Portal. These parties may create alerts and/or reminders in the system, and system will communicate said alerts and/or reminders to Patron via one or more of several methods allowed by the Patron App, Patron Software, and/or Patron Portal, including but not limited to emails, text messages, pop-up notifications, sounds, vibrations, messages delivered within or through the Patron App, Patron Software, and/or Patron Portal.

By way of further example, a Venue, Television Network, Television Channel, Cable Network, Satellite Network, Radio Network, Sports Team, Sports League, content producer, beverage producer, food producer, food distributor, beverage distributor, advertiser, etc. may wish to entice Patrons to extend their current media content experience by offering, suggesting and/or recommending specified media content, with the offered, suggested, and/or recommended media content being based on media content specified in the Patron-to-Presentation Reservation, and/or the media content currently being enjoyed by Patron, and/or media content that is scheduled to be presented simultaneously in the Venue specified in the Patron-to-Presentation Reservation. Said offered, suggested, and/or recommended media content may be based on media content that matches either the Patron's expressly stated preferences as captured in the Patron Profile, the Patron's implied preferences as captured in the Patron's Reservation History, as determined based on content reservations of other Patrons who enjoyed content similar to the content specified in the Patron-to-Presentation Reservation, or as determined based on Patron-to-Presentation Reservations of other Patrons who have historically enjoyed and/or are currently enjoying media content similar to the media content specified in the Patron-to-Presentation Reservation. If said offered, suggested, and/or recommended media content will be available for Patron to experience at the same Venue, and said media content is scheduled to be available immediately prior to, concurrently, or after the media content specified in the Patron-to-Presentation Reservation, then said media content may entice Patron to arrive at the Venue earlier and/or stay longer at the Venue. These parties may use the system to communicate and/or recommend the availability, nature, scope, timing, location, cost, benefits, and/or other facets of specified media content to Patrons via the Patron App, Patron Software, and/or Patron Portal. These parties may create alerts and/or reminders in the system, and system will communicate said alerts and/or reminders to Patron via one or more of several methods allowed by the Patron App, Patron Software, and/or Patron Portal, including but not limited to emails, text messages, pop-up notifications, sounds, vibrations, messages delivered within or through the Patron App, Patron Software, and/or Patron Portal.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable storage medium and computer-readable storage medium refer to any computer program product, apparatus and/or device (e.g., magnetic discs, optical disks, memory, Programmable Logic Devices (PLDs)) used to provide machine instructions and/or data to a programmable processor, including a machine-readable storage medium that receives machine instructions as a machine-readable signal. The term machine-readable signal refers to any signal used to provide machine instructions and/or data to a programmable processor. A machine-readable storage medium does not include a machine-readable signal.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball or touchscreen) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any implementation or of what may be claimed, but rather as descriptions of features that may be specific to particular embodiments of particular implementations. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Various modifications and changes can be made to the subject matter described herein without following the example embodiments and applications illustrated and described, and without departing from the true spirit and scope of the present disclosure, which is set forth in the following claims.

What is claimed is:

1. A computer-implemented method for scheduling and controlling the presentation of media content at a venue that has media devices including one or more media source devices connected to a network at the venue and connected to one or more media presentation devices, the method comprising:

receiving at a schedule management server:
      electronic programming data including a list of media content items that are available for presentation at the venue, a respective media source and any respective time-periods for each of the media content items, and
      venue data including information identifying the one or more media source devices, wherein the one or more media source devices are configured to provide media content received from a respective media source to one or more media presentation devices for output;
   providing a venue control module at the venue, wherein the venue control module is provided for integration in the venue network and is configured to communicate with the one or more media devices via the venue network and communicate with the server via a communications network connection, and wherein the venue control module is one or more of: a device operatively connected to the venue network and a software module executed by one or more of the media devices which are operatively connected to the venue network;
   maintaining, with the server based on the electronic programming data and the venue data, a venue programming schedule identifying scheduled media content items for presentation at the venue during respective time periods;
   generating, according to the venue programming schedule, control instructions for causing one or more of the media devices at the venue to output the scheduled media content items at the venue during respective time periods, wherein the control instructions are generated by one or more of the schedule management server based on the venue data and the venue control module based on venue settings concerning a configuration of the media devices at the venue;
   providing the control instructions at the venue control module; and
   issuing, by the venue control module according to the control instructions, control parameters to one or more of the media devices, wherein the control parameters cause one or more of the media devices to transition to a respective state that is suitable for presenting a particular scheduled media content item at the venue at a respective execution time.

2. The method of claim 1, wherein a media source is one or more of: a local or remote storage medium having media content items stored persistently therein, an internet-based media content source configured to stream media content items to the venue over a communications network, a remote media source configured to transmit media content items to the venue via a cable-based communications channel, and a remote media source configured to transmit media content items to the venue via a satellite-based communications channel.

3. The method of claim 1, wherein the venue data stored by the schedule management server comprises one or more of: access rights that control which media content items are available for presentation at the venue, venue-defined limitations relating to the availability of media content items for presentation at the venue, information usable to map connectivity between the one or more media source devices and the one or more presentation devices within the venue, and the configuration of one or more of the media devices at the venue.

4. The method of claim 1, wherein the venue settings define one or more of: a configuration of one or more of the media source devices and the respective media sources that are accessible therewith, a configuration of the one or more presentation devices, and information describing the connectivity between each of the one or more media source devices and the one or more presentation devices.

5. The method of claim 4, wherein the venue settings include one or more of:
   credentials for accessing respective media sources using the one or more media source devices, venue-defined limitations relating to the availability of media content items for presentation at the venue, a configuration of the venue network interconnecting one or more of the venue devices, a configuration of a router connected to the venue network.

6. The method of claim 1, wherein the step of generating the control instructions comprises:
   identifying based on the venue programming schedule, a particular media source device for providing a particular scheduled media content item identified in the venue programming schedule to a presentation device during a particular respective time period; and
   wherein the step of issuing further comprises: transmitting, by the venue control module, a command that includes the control parameters defined to cause the particular media source device to, at a prescribed execution time, receive the particular media content item from the respective media source and provide the particular media content item to the presentation device, wherein the prescribed execution time corresponds to the respective time period.

7. The method of claim 6, further comprising: defining the control parameters, wherein the control parameters are defined to cause the particular media source device to perform one or more of the following actions: tune to a particular channel or frequency, access a particular internet-protocol address, provide credentials useable to access the particular media content item to the respective media source, download the particular media content item from the respective media source.

8. The method of claim 7, further comprising:
wherein the control parameters include one or more of:
media source device tuning settings, media source configuration settings, routing settings for a network switch connected to the venue network, audio source tuning settings, audio source selection settings, audio volume settings, content management system settings, software and middleware settings, and venue network settings.

9. The method of claim 6, further comprising:
identifying, by the venue control module based on the venue settings and the venue programming schedule, a particular presentation device that is connected to the particular media source device and that is available for outputting the particular scheduled media content item; and
generating a command that is addressed to the particular presentation device and causes the particular presentation device to transition to an operational state that is suitable for outputting the particular scheduled media content provided by the particular media source device.

10. The method of claim 6, wherein the one or more presentation devices are communicatively connected to the one or more media source devices in a one-to-one relationship and configured to output media content items received directly from the one or more media source devices, and wherein generating the control instructions further comprises:
defining the control parameters for transmission to the particular media source device, the media source control parameters including one or more of: a channel setting and a channel change command.

11. The method of claim 6, wherein a plurality of presentation devices are connected to a plurality of media source devices in a many-to-many relationship and wherein generating the control instructions further comprises:
identifying, based on the received venue programming schedule and based on the venue settings, one or more media source devices among the plurality of media source devices and one or more presentation devices among the plurality of presentation devices that are suitable for outputting the particular scheduled media content item identified in the venue programming schedule during a particular respective time period;
for each of the identified one or more media source devices, defining respective media source device control parameters for transmission to a respective media source device, wherein the media source control parameters include one or more of: a channel setting and a channel change command;
for each of the identified one or more presentation devices, defining respective presentation device control parameters that are transmitted to a respective presentation device, wherein the presentation device control parameters define a source setting that causes the particular presentation device to output media content items provided by at least one of the identified one or more media source devices.

12. The method of claim 11, wherein the media devices include a matrix switch and wherein the plurality of presentation devices are indirectly connected to the plurality of media source devices via the matrix switch, and wherein generating the command instructions comprises:
determining, based on the venue settings and the identified one or more media source devices and the identified one or more presentation devices, matrix switch routing settings for routing the media content items provided by the identified one or more media source devices to the identified one or more presentation devices.

13. The method of claim 6, wherein a particular presentation device is connected to a plurality of media source devices in a one-to-many relationship and wherein generating the control instructions further comprises:
identifying, based on the received venue programming schedule and based on the venue settings, a particular media source device among the plurality of media source devices that is suitable for outputting the particular scheduled media content item identified in the venue programming schedule during a particular respective time period;
defining media source control parameters that are transmitted to the particular media source device, wherein the media source control parameters include one or more of: a channel setting and a channel change command;
defining, based on the identified one or more media sources and venue settings concerning the connectivity between the plurality of media source devices and the particular presentation device, presentation device control parameters that are transmitted to the particular presentation device, wherein the presentation device control parameters include one or more of: a source setting, an audio volume setting and a closed caption instruction.

14. The method of claim 6, wherein at least a portion of the venue settings are stored by one or more of the venue control module and the schedule management server, and wherein the control instructions are generated by one or more of the venue control module and the schedule management server.

15. The method of claim 6, further comprising:
reporting, by the venue control module to the schedule management server, a status of the one or more media source devices and the one or more presentation devices at the venue relating to presentation of a particular media content item at the venue; and
dynamically updating, by the schedule management server based on the reported status, the venue programming schedule to reflect the presentation of the particular media content item.

16. The method of claim 1, further comprising:
receiving one or more of the venue settings at the venue control module from a venue user device, and wherein the venue settings are stored by the venue control module in a storage medium; and
receiving, at least a portion of the venue data at the schedule management server from one or more of the venue user device and the venue control module.

17. The method of claim 1, the maintaining step comprises:
receiving, at the schedule management server from a user computing device over a communications network, a scheduling request that requests presentation of a media content item at the venue during a respective time period;
verifying, based on the venue programming schedule and the venue data, that at least one of the one or more media source devices is available to facilitate presentation of the requested media content item at the venue during the respective time period; and
based on the verification of the requested media content item, updating the venue programming schedule to include the media content item requested for presentation at the venue during the respective time period.

18. A system for scheduling and controlling the presentation of media content at a venue having a network of media devices including media presentation devices and one or more media source devices connected to a local network at the venue, wherein the one or more media source devices are configured provide media content received from a respective media source to one or more of the media presentation devices for output, the system comprising:
a schedule management server comprising:
a processor, a non-transitory computer readable storage medium and one or more software modules in the form of encoded instructions that are executable by the processor, the software modules including:
a communications module that configures the schedule management server to receive electronic programming data and venue data from one or more remote computing devices over a communications network, wherein the electronic programming data includes a list of media content items that are available for presentation at the venue, a respective media source and any respective time-periods for each of the media content items, and wherein the venue data includes information identifying the one or more media source devices at the venue,
a scheduling module that configures the schedule management server to maintain, based on the electronic programming data and the venue data, a venue programming schedule identifying scheduled media content items for presentation at the venue during respective time periods, and
a content change manager that configures the schedule management server to transmit content change instructions based on the venue programming schedule over the communication network to a venue; and
a venue control module located at the venue for automatically coordinating the output of the scheduled media content items at the venue during respective time periods according to the venue programming schedule, wherein the venue control module is integrated within the venue network and is configured to communicate with one or more of the media devices at the venue over the venue network and communicate with the schedule management server over the communications network, and wherein the venue control module is further configured to:
maintain, in a storage medium, venue settings concerning a configuration of the media devices at the venue,
generate, according to the received content change instructions and the venue settings, control instructions that transition one or more of the media devices to a respective state that is suitable for presenting a particular scheduled media content item at the venue at a respective execution time, and
transmit the control instructions to one or more of the media devices over the venue network.

19. The system of claim 18, wherein the venue control module is one or more of: a device operatively connected to the venue network including a processor, a local storage medium and a communications interface, and a software-based module that is executing in at least one of the media devices that are operatively connected to the venue network.

20. The system of claim 18, wherein the venue control module is configured to:
receive the content change instructions from the content change manager over a first communications network connection, wherein the first communications network connection is different from the venue network,
convert the content change instructions into control instructions having a format that is executable by the one or more media devices, and
transmit the control instructions to the one or more of the media devices over the venue network, whereby the venue control module enables the content change instructions that are received over the first communications network channel to be implemented by the one or more media devices irrespective of whether the one or more media devices are connected to the first communications channel.

21. The system of claim 18,
wherein the venue data stored by the schedule management server comprises one or more of: access rights that control which media content items are available for presentation at the venue, venue-defined limitations relating to the availability of media content items for presentation at the venue, information usable to map connectivity between the one or more media source devices and the one or more presentation devices within the venue, and specifications for one or more of the media devices at the venue; and
wherein the venue settings include one or more of: specifications for the one or more media source devices, specifications for the respective media sources that are accessible using the one or more media source devices, specifications for the one or more presentation devices, venue network specifications, and information describing the connectivity between each of the one or more media source devices and the one or more presentation devices.

22. The system of claim 18, wherein the venue control module is configured to generate the control instructions by:
identifying based on the control instructions, a particular media source device for providing a particular scheduled media content item to a presentation device during a particular respective time period; and
defining one or more control parameters that cause the particular media source device to, at a prescribed execution time, receive the particular media content item from the respective media source and provide the particular media content item to the presentation device, wherein the prescribed execution time corresponds to the respective time period.

23. The system of claim 22, wherein the venue control module is further configured to generate the control instructions by:
identifying, based on the venue settings and the control instructions, a particular presentation device that is available for outputting the particular scheduled media content item during the particular respective time period; and
defining one or more control parameters that cause the particular presentation device to transition to an operational state that is suitable for outputting the particular scheduled media content provided by the particular media source device.

24. The system of claim 23, wherein the control parameters include one or more of:
media source device tuning settings, routing settings for a network switch connected to the venue network, audio source selection settings for a presentation device, media source selection settings for a presentation device, audio volume settings for a presentation device; and wherein the control instructions are generated for specific media devices among the plurality of media devices.

25. The system of claim 23, wherein the media devices include a matrix switch and wherein a plurality of presentation devices are indirectly connected to a plurality of media source devices via the matrix switch, and wherein the venue control module is further configured to:
- identify the one or more media source devices and the one or more presentation devices based on specifications for the matrix switch; and
- define, based on specifications for the matrix switch, matrix switch routing settings for routing the media content items provided by the identified one or more media source devices to the identified one or more presentation devices.

26. The system of claim 18,
wherein the communications module configures the schedule management server to receive, from a user computing device over the communications network, a scheduling request that requests presentation of a media content item at the venue during a respective time period; and wherein the scheduling module further configures the schedule management server to verify, according to the venue programming schedule and the venue data, that at least one of the one or more media source devices is available to facilitate presentation of the requested media content item at the venue during the respective time period, and update the venue programming schedule to include the requested media content item based on the verification.

27. The system of claim 18, wherein the venue control module is configured to report to the schedule management server, a status of the one or more media source devices and the one or more presentation devices at the venue relating to presentation of a particular media content item at the venue; and wherein the scheduling module further configures the schedule management server to, based on the reported status, dynamically update the venue programming schedule to reflect the presentation of the particular media content item and at least the status of the one or more media source devices.

* * * * *